United States Patent

Watson et al.

[11] Patent Number: 4,604,128
[45] Date of Patent: Aug. 5, 1986

[54] HERBICIDAL CYCLOHEXANE-1,3-DIONE DERIVATIVES

[75] Inventors: Keith G. Watson, Blackburn North; John D. Wishart, Mordialloc; Graeme J. Farquharson, Carlton; Graham J. Bird, Ascot Vale; Lindsay E. Cross, Maribyrnong, all of Australia

[73] Assignee: ICI Australia Limited, Melbourne, Australia

[21] Appl. No.: 774,525

[22] Filed: Sep. 10, 1985

[30] Foreign Application Priority Data

Sep. 25, 1984 [AU] Australia .............................. PG7297

[51] Int. Cl.$^4$ ................. C07D 335/04; C07D 221/12; C07D 311/80; A01N 43/00; A01N 43/40; A01N 33/08; C07C 131/00

[52] U.S. Cl. ........................................ 71/88; 560/251; 560/252; 71/90; 562/440; 71/94; 260/502.6; 546/109; 71/98; 558/48; 558/253; 71/99; 558/405; 71/100; 558/414; 71/103; 71/105; 71/106; 71/107; 71/121; 549/12; 549/26; 549/27; 549/43; 549/44; 549/48; 549/280; 549/354; 549/388; 549/460; 549/461; 564/74; 564/85; 564/86; 564/99; 564/164; 564/168; 564/222; 564/223; 560/5; 560/35; 560/107

[58] Field of Search ................. 564/256, 85, 86, 99, 564/168, 222, 223, 74, 164; 71/88, 90, 94, 98, 99, 100, 103, 105, 106, 107, 121; 549/12, 26, 27, 43, 44, 48, 280, 354, 388, 460, 461; 560/5, 35, 107, 251, 252; 562/440; 260/502.6; 546/109; 558/48, 253, 405, 414

[56] References Cited

U.S. PATENT DOCUMENTS 4,440,566 4/1984 Luo ................................ 71/121

*Primary Examiner*—Natalie Trousof
*Assistant Examiner*—L. Hendriksen
*Attorney, Agent, or Firm*—Cushman, Darby & Cushman

[57] ABSTRACT

The invention concerns novel compounds of the formula I

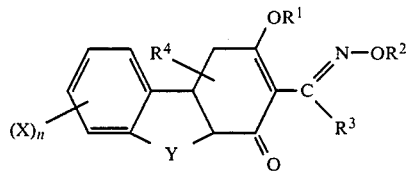

wherein:
m is an integer selected from 1 to 4;
n is zero or an integer selected from 1 to 4;
X are selected from halogen, nitro, cyano, alkyl, substituted alkyl, hydroxy, alkoxy, alkylthio, sulfamoyl, substituted sulfamoyl, amino, substituted amino, the group $-(CH_2)_pC(=A)Z$ in which p is zero or one A is oxygen or sulfur, and Z is hydrogen, hydroxy, alkoxy, alkylthio, alkyl, substituted alkyl, amino or substituted amino, the group $-NHC(=B)NR^7R^8$ in which B is oxygen or sulfur and $R^7$ and $R^8$ are hydrogen or alkyl;
$R^1$ is selected from hydrogen, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl; and
$R^4$ is selected from hydrogen, halogen, alkyl, cyano and alkoxycarbonyl.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

13 Claims, No Drawings

HERBICIDAL CYCLOHEXANE-1,3-DIONE DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464,655 and its equivalents such as UK Pat. No. 1,461,170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, (1980), a new cyclohexane-1,3-dione grass herbicide code named NP 55 (2-N-ethoxybutrimidoyl)-5-(2-ethylthiopropyl)-3-hydroxy-2-cyclohexen-1-one) was announced. This compound is disclosed in Australian Pat. No. 503,917 and its equivalents.

It is also disclosed in Australian Pat. No. 464,655 and its equivalents such as U.S. Pat. No. 3,950,420 that bicyclic fused diones such as 2-]1-(ethoxyamino) propylidene]-4,5-tetramethylenecyclohexane-1,3-dione have certain useful herbicidal properties.

It has now been found that a new group of fused tricyclic 1,3 dione derivatives exhibit particularly useful herbicidal activity.

Accordingly the invention provides a compound of formula I or an isomer thereof:

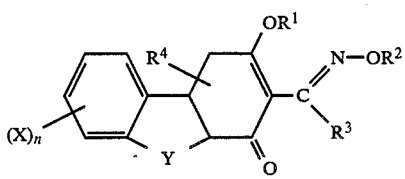

wherein:
n is zero or an integer selected from 1 to 4;
Y is a linking group selected from the group consisting of:
$-(CH_2)_l-$; $-CH(CH_3)-$; $-C(CH_3)_2-$; $-CH(CH_3)CH_2-$; $-G(CH_2)_m-$; $-CH_2GCH_2-$; $-C(G)(CH_2)_m-$; $-GC(G)-$; and $-NHC(G)-$;
wherein:
G is selected from oxygen and sulfur;
l is an integer selected from 1 to 3; and
m is zero or an integer selected from 1 and 2;
X, which may be the same or different, are independently selected from the group consisting of: halogen; nitro; cyano; $C_1$ to $C_6$ alkyl; $C_1$ to $C_6$ alkyl substituted with halogen or cyano; hydroxy; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group $-(CH_2)_pC(=A)Z$ wherein p is zero or one, A is selected from oxygen and sulfur, and Z is selected from the group consisting of hydrogen, hydroxy, $C_1$ to $C_6$ alkoxy, $C_1$ to $C_6$ alkylthio, amino, N-($C_1$ to $C_6$ alkyl)amino, N,N-di($C_1$ to $C_6$ alkyl)amino, N-($C_1$ to $C_6$ alkanoyl)amino, $C_1$ to $C_6$ alkyl, and $C_1$ to $C_6$ haloalkyl; the group $-NR^5R^6$ wherein $R^5$ and $R^6$ are independently selected from the group consisting of hydrogen, $C_1$ to $C_6$ alkyl, $C_2$ to $C_6$ alkanoyl, $C_2$ to $C_6$ haloalkanoyl, $C_1$ to $C_6$ alkylsulfonyl, and benzoyl; the group $-NHC(=B)NR^7R^8$ wherein B is selected from oxygen and sulfur and $R^7$ and $R^8$ are independently selected from hydrogen and $C_1$ to $C_6$ alkyl; and the group $-(CH_2)_q-$ which bridges two adjacent carbon atoms of the benzene ring and where q is an integer selected from 3 or 4;

$R^1$ is selected from the group consisting of: hydrogen; an acyl group; and an inorganic or organic cation;
$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_3$ to $C_6$ haloalkynyl; and substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, $C_1$ to $C_6$ alkyl, $C_1$ to $C_6$ haloalkyl, $C_1$ to $C_6$ alkoxy, and $C_1$ to $C_6$ alkylthio;
$R_3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and
$R_4$ is selected from the group consisting of: hydrogen; halogen; cyano; $C_1$ to $C_6$ alkyl; and ($C_1$ to $C_6$ alkoxy) carbonyl.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N^+$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chpsen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

The compounds of the invention may exist in either of the two isomeric forms shown below or a mixture of these two isomeric forms.

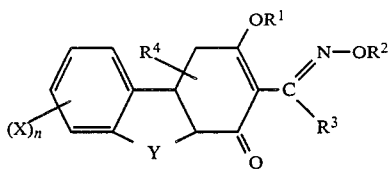

Ia

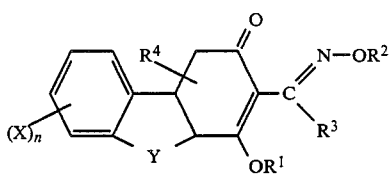

Ib

It should be recognized that when $R^1$ is hydrogen the compounds of the invention may exist in any one, or in any mixture, of the four tautomeric forms shown below.

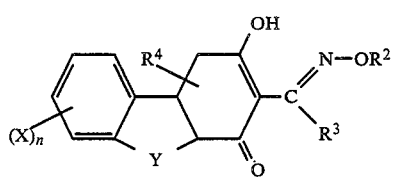

IIa

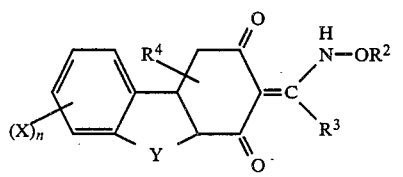

IIb

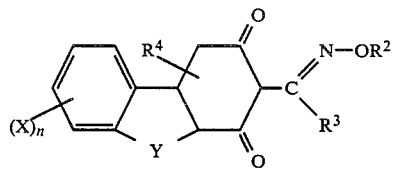

IIc

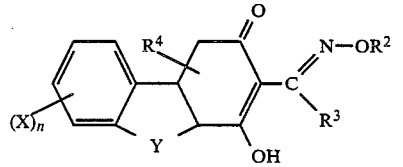

IId

Preferred compounds of the invention include those compounds of formula I wherein:

Y is selected from one of the groups $CH_2$, $CH_2CH_2$, $CH_2CH_2CH_2$, $OCH_2$, $SCH_2$, $CH_2O$ and $CH_2S$;

n is zero or an integer selected from 1 to 4;

X, which may be the same or different, are independently selected from the group consisting of: halogen; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; the group —$(CH_2)_pC(=A)Z$ wherein p is zero or one, A is oxygen or sulfur and Z is selected from the group consisting of hydroxy, $C_1$ to $C_6$ alkoxy, $C_1$ to $C_6$ alkylthio, amino, N,N-di($C_1$ to $C_6$ alkyl)amino, $C_1$ to $C_6$ alkyl; the group —$NHR^5$ wherein $R^5$ is selected from the group consisting of hydrogen, $C_2$ to $C_6$ alkanoyl, $C_2$ to $C_6$ haloalkanoyl, $C_1$ to $C_6$ alkylsulfonyl and benzoyl; and the group —$(CH_2)_q$— which bridges two adjacent carbon atoms of the benzene ring and wherein q is an integer selected from 3 or 4;

$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra(alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_3$ to $C_6$ haloalkynyl;

$R^3$ is selected from $C_1$ to $C_6$ alkyl;

$R^4$ is hydrogen.

More preferred compounds of the invention include those compounds of formula I wherein:

Y is selected from the group consisting of $CH_2$, $CH_2CH_2$, $CH_2CH_2CH_2$, $OCH_2$, $SCH_2$, $CH_2O$ and $CH_2S$;

n is zero or an integer selected from 1 to 4;

X, which may be the same or different, are independently selected from the group consisting of: halogen; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl)sulfamoyl; $C_2$ to $C_6$ alkanoyl; $C_1$ to $C_6$ haloalkanoylamino; and the group —$(CH_2)_q$— which bridges two adjacent carbon atoms of the benzene ring and wherein q is an integer selected from 3 or 4;

$R^1$ is selected from the group consisting of hydrogen, $C_2$ to $C_6$ alkanoyl, and the alkali and alkaline earth metals;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_2$ to $C_6$ alkynyl;

$R^3$ is selected from the group consisting of $C_1$ to $C_6$ alkyl; and $R^4$ is hydrogen.

Even more preferred compounds of the invention include those compounds of formula I wherein:

Y is selected from the group consisting of $CH_2$, $CH_2CH_2$, $CH_2CH_2CH_2$, $OCH_2$, $SCH_2$, $CH_2O$ and $CH_2S$;

n is an integer selected from 1 to 4;

X, which may be the same or different, are independently selected from the group consisting of: halogen, methyl, methoxy, methylthio, methylsulfamoyl, acetyl, propionyl, trifluoroacetylamino and the groups —$(CH_2)_3$— and —$(CH_2)_4$— which bridge two adjacent carbon atoms of the benzene ring;

$R^1$ is selected from hydrogen and the alkali metals;

$R^2$ is selected from the group consisting of $C_2$ to $C_3$ alkyl, $C_2$ to $C_3$ haloalkyl, allyl, haloallyl and propargyl;

$R^3$ is selected from $C_2$ to $C_3$ alkyl; and $R^4$ is hydrogen.

Specific examples of the compound of the invention include those compounds detailed in Tables 1a and 1b below.

TABLE 1a

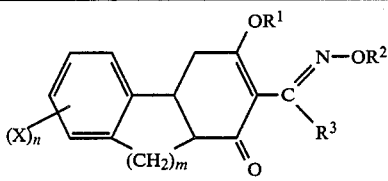

| Compound No | (X)$_n$ | m | $R^1$ | $R^2$ | $R^3$ |
|---|---|---|---|---|---|
| 1 | H | 2 | H | CH$_2$CH$_3$ | CH$_2$CH$_3$ |
| 2 | H | 2 | H | CH$_2$CH$_3$ | CH$_2$CH$_3$ |
| 3 | H | 2 | H | CH$_2$CH$_3$ | CH$_2$CH$_3$ |
| 4 | H | 2 | H | CH$_2$CH$_3$ | CH$_2$CH$_2$CH$_3$ |
| 5 | H | 2 | H | CH$_2$CH$_3$ | CH$_2$CH$_2$CH$_3$ |
| 6 | H | 2 | H | CH$_2$CH$_3$ | CH$_2$CH$_2$CH$_3$ |
| 7 | 6-CH$_3$ | 2 | H | CH$_2$CH$_3$ | CH$_2$CH$_3$ |
| 8 | 6-CH$_3$ | 2 | H | CH$_2$CH$_3$ | CH$_2$CH$_3$ |
| 9 | 7-CH$_3$ | 2 | H | CH$_2$CH$_3$ | CH$_2$CH$_3$ |
| 10 | 6-CH(OH)CH$_3$ | 2 | H | CH$_2$CH$_3$ | CH$_2$CH$_3$ |
| 11 | 6-COCH$_3$ | 2 | H | CH$_2$CH$_3$ | CH$_2$CH$_3$ |
| 12 | 6,7-(CH$_3$)$_2$ | 2 | H | CH$_2$CH$_3$ | CH$_2$CH$_3$ |
| 13 | 6,8-(CH$_3$)$_2$ | 2 | H | CH$_2$CH$_3$ | CH$_2$CH$_3$ |
| 14 | 5,6,7,8-(CH$_3$)$_4$ | 2 | H | CH$_2$CH$_3$ | CH$_2$CH$_3$ |
| 15 | 6-(CH$_3$O)—5,7-(CH$_3$)$_2$ | 2 | H | CH$_2$CH$_3$ | CH$_2$CH$_3$ |
| 16 | 6-(CH$_3$O)—5,7,8-(CH$_3$)$_3$ | 2 | H | CH$_2$CH$_3$ | CH$_2$CH$_3$ |
| 17 | 8-(CH$_3$O)—5,6,7-(CH$_3$)$_3$ | 2 | H | CH$_2$CH$_3$ | CH$_2$CH$_3$ |
| 18 | 6,7-(CH$_2$)$_3$—5,8-(CH$_3$)$_2$ | 2 | H | CH$_2$CH$_3$ | CH$_2$CH$_3$ |
| 19 | 5,7-(CH$_3$)$_2$ | 2 | H | CH$_2$CH$_3$ | CH$_2$CH$_3$ |
| 20 | 5,6,7-(CH$_3$)$_3$ | 2 | H | CH$_2$CH$_3$ | CH$_2$CH$_3$ |
| 21 | 6,8-(CH$_3$)$_2$—7-(CH$_3$)$_2$NSO$_2$ | 2 | H | CH$_2$CH$_3$ | CH$_2$CH$_3$ |
| 22 | 6-(CH$_3$O)—5,7-(CH$_3$)$_2$—8-NO$_2$ | 2 | H | CH$_2$CH$_3$ | CH$_2$CH$_3$ |
| 23 | 7-CH$_3$CO—6,8-(CH$_3$)$_2$ | 2 | H | CH$_2$CH$_3$ | CH$_2$CH$_3$ |
| 24 | 8-CH$_3$CO—5,6,7-(CH$_3$)$_3$ | 2 | H | CH$_2$CH$_3$ | CH$_2$CH$_3$ |
| 25 | 5,6,7,8-(CH$_3$)$_4$ | 2 | H | CH$_2$CH=CH$_2$ | CH$_2$CH$_3$ |
| 26 | 6,8-(CH$_3$)$_2$ | 2 | H | CH$_2$C≡CH | CH$_2$CH$_3$ |
| 27 | H | 2 | Na | CH$_2$CH$_3$ | CH$_2$CH$_2$CH$_3$ |
| 28 | H | 1 | H | CH$_2$CH$_3$ | CH$_2$CH$_3$ |
| 29 | 5,7-(CH$_3$)$_2$ | 1 | H | CH$_2$CH$_3$ | CH$_2$CH$_3$ |
| 30 | 5,6,7,8-(CH$_3$)$_4$ | 1 | H | CH$_2$CH$_3$ | CH$_2$CH$_3$ |
| 31 | 5,6,7,8-(CH$_3$)$_4$ | 1 | H | CH$_2$CH$_3$ | CH$_2$CH$_3$ |
| 32 | 6-(CH$_3$O)—5,7-(CH$_3$)$_2$ | 1 | H | CH$_2$CH$_3$ | CH$_2$CH$_3$ |
| 33 | 5,6,7,8-(CH$_3$)$_4$ | 1 | H | CH$_2$CH$_2$F | CH$_2$CH$_3$ |
| 34 | H | 3 | H | CH$_2$CH$_3$ | CH$_2$CH$_2$CH$_3$ |

TABLE 1b

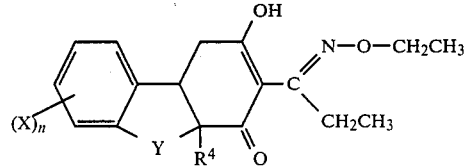

| Compound No. | (X)$_n$ | Y | $R^4$ |
|---|---|---|---|
| 35 | H | —O—C(=O)— | H |
| 36 | 7-CH$_3$ | —C(=O)CH$_2$— | CO$_2$CH$_2$CH$_3$ |
| 37 | H | —O— | H |
| 38 | 5,7-(CH$_3$)$_2$ | —O— | H |
| 39 | H | —OCH$_2$— | H |
| 40 | 5,7-(CH$_3$)$_2$ | —CH$_2$S— | H |
| 41 | 5,6,7,8-(CH$_3$)$_4$ | —CH$_2$S— | H |
| 42 | 5,7-(CH$_3$)$_2$ | —OCH$_2$CH$_2$— | CO$_2$CH$_2$CH$_3$ |

It will be evident to those skilled in the art that the compounds of formula I can exist in two isomeric forms depending on the stereochemistry on the cyclohexenone ring at the junction of the rings. In Table 1a compounds no 1, 4, 9 to 13, 21, 23, 26, 27, 34 to 36 and 39 comprise a mixture of cis- and trans- isomers; compounds no 3, 6, 8, 14, 15, 16, 17, 18, 19, 20, 22, 24, 25, 28, 29, 30, 31, 32, 33, 37, 38, 40 and 41 are believed to be trans- iosmers; and compounds no 2, 5 and 7 are believed to be cis- isomers.

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a tricyclic 1,3-dione derivative of formula VIII or IX. This preparation may be carried out by a variety of methods including:

(i) intramolecular Michael condensation of an α,β-unsaturated ketone of formula V, preferably in the presence of a base, to give a tricyclic 1,3-dione derivative of formula IX;

(ii) reacting an α,β-unsaturated ketone of formula VI with a malonic acid ester of formula VII, in the presence of a base to give an intermediate of formula VIII which may be isolated or hydrolysed directly, preferably in the presence of a base, to give a tricyclic 1,3-dione derivative of formula IX. Alternatively the intermediate of formula VIII may be acylated without isolation as described in part B below.

Part B involves the acylation of a compound of formula IX to give a 2-acyl tricyclic 1,3-dione derivative of formula XIII. Alternatively Part B involves the acylation of a compound of formula VIII to give a 2-acyl tricyclic 1,3-dione of formula XIV which may be hydrolysed directly, preferably in the presence of a base, to give a 2-acyl tricyclic 1,3-dione derivative of formula XIII. The acylation reaction may be carried out by reacting a tricyclic 1,3-dione derivative of formula VIII or IX with:

(iii) an acid anhydride of formula X in the presence of either an alkali metal salt of the corresponding acid of formula XI or an alkoxide salt of formula XII, wherein M is an alkali metal ion and R is $C_1$ to $C_6$ alkyl;

(iv) an acid anhydride of formula X in the presence of the corresponding acid of formula XV, preferably in the presence of a Lewis acid or strong proton acid catalyst;

(v) an alkali or alkaline earth metal hydride followed by reaction with an acid anhydride of formula X or an acid halide of formula XVI;

(vi) an acid anhydride of formula X in the presence of a strong organic base such as 4-dimethylaminopyridine or imidazole.

Alternatively, this acylation reaction may be carried out by:

(vii) reacting a tricyclic 1,3-dione derivative of formula VIII or formula IX with an acid halide of formula XVI in the presence of a base to give an intermediate 0-acyl derivative of formula XVII; and (viii) reacting the intermediate of formula XVII with a Lewis acid or strong proton acid catalyst;

(ix) reacting the intermediate of formula XVII with a suitable strong organic base such as 4-dimethylaminopyridine or imidazole.

Part C involves the formation of a compound of the invention of formula I wherein $R^1$ is hydrogen, that is a compound of formula II. This reaction may be carried out either by reacting a 2-acyl tricyclic 1,3-dione derivative of formlua XIII with:

(xi) an alkoxyamine derivative of formula XVIII, or (xii) hydroxylamine to give an intermediate oxime derivative of formula XIX and reacting that intermediate oxime derivative of formula XIX with an alkylating agent of formula XX, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part D involves the formation of a compound of the invention of formula I wherein $R^1$ is a substituent other than hydrogen.

Compounds of the invention of formula I, wherein $R^1$ forms an acyl derivative of a compound of formula II, may be prepared from the corresponding compounds of the invention of formula II by reacting with an acylation reagent of formula XXI.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting a 2-acyl tricyclic 1,3-dione derivative of formula XIII with an alkoxyamine derivative of formula XVIII to give a compound of the invention of formula II or reacting the 2-acyl tricyclic 1,3-dione derivative of formula XIII with hydroxylamine and alkylating the oxime intermediate of formula XIX with an alkylating agent of formula XX, wherein L is a leaving group, to give a compound of the invention of formula II; and optionally reacting the compound of the invention of formula II with a compound of formula XXI wherein L is a leaving group, to give a compound of the invention of formula I.

The structures of the compounds described above are detailed on the following pages.

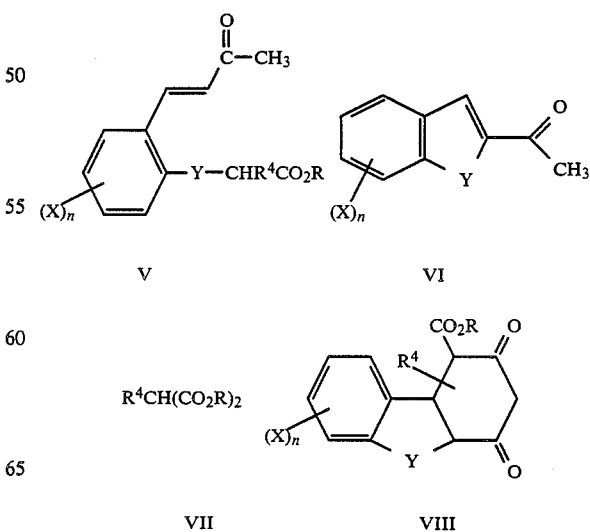

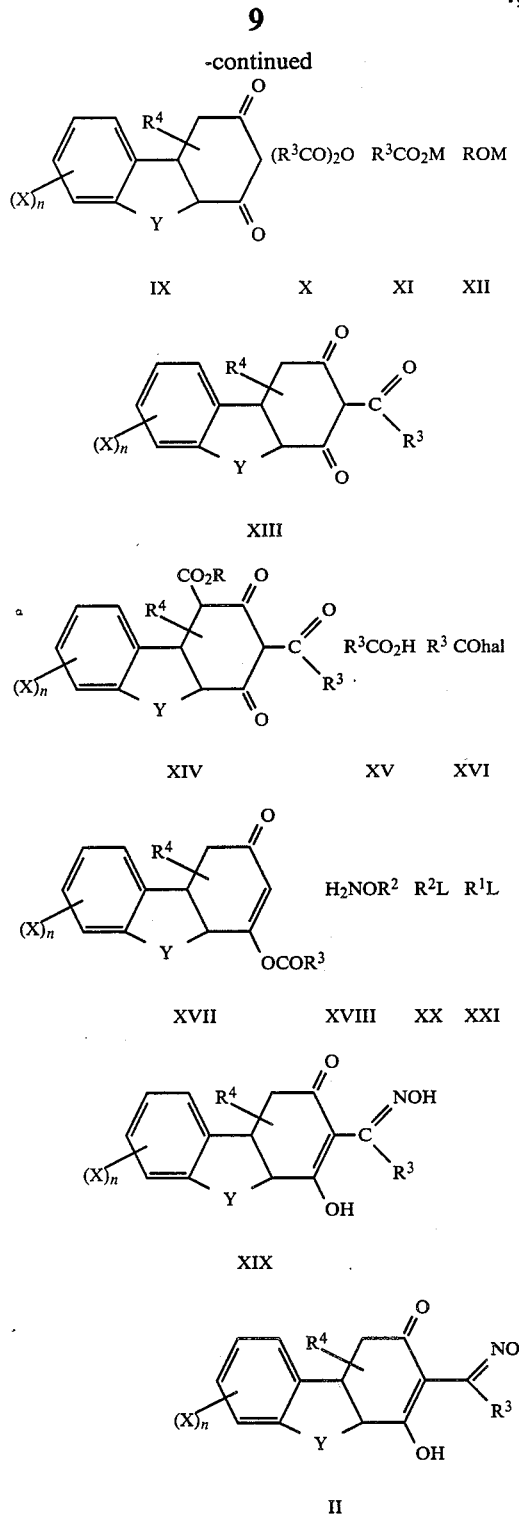

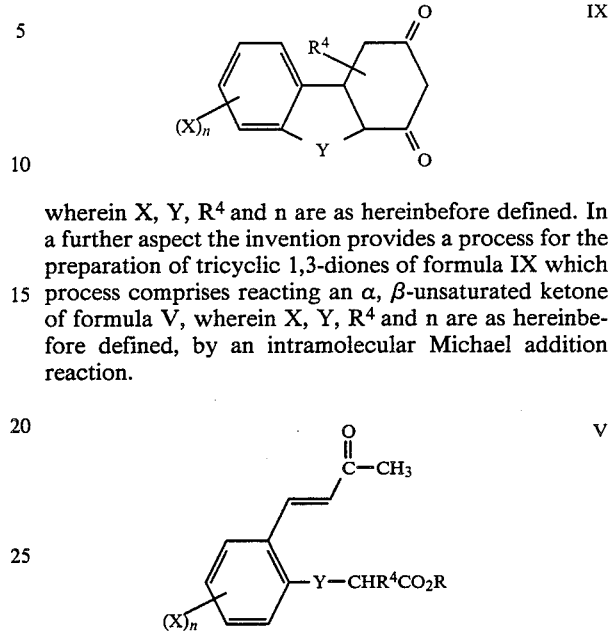

aspect the invention provides a compound of formula IX wherein X, Y, $R^4$ and n are as hereinbefore defined. In a further aspect the invention provides a process for the preparation of tricyclic 1,3-diones of formula IX which process comprises reacting an α, β-unsaturated ketone of formula V, wherein X, Y, $R^4$ and n are as hereinbefore defined, by an intramolecular Michael addition reaction.

Certain of the intermediate compounds of formulae VI, VIII, IX, XIII, XIV, XVII and XIX are novel compounds and therefore in further embodiments the invention provides novel compounds of formula VI, VIII, IX, XIII, XIV, XVII and XIX and processes for the preparation thereof. For example, only one of the tricyclic diones for formula IX used in the preparation of the compounds of the invention of formula I, namely, 1,2, 3, 4, 4a, 9b -hexahydrodibenzofuran -2,4-dione, has previously been described. Accordingly, in a further The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in vegetable and cereal crops, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) and in general are more effective when applied to the plant post-emergence than pre-emergence.

The compounds of formula I may be used on their own to inhibit the growth of, severely damage, or kill plants but are preferably used in the form of a composition comprising a compound of the invention in admixture with a carrier comprising a solid or liquid diluent.

Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium niirate and urea; natural products of vegetable origin such as, for example, grain meals and flours, bark metals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate tne dispersion of the active ingredient in liquid.

Examples of surface active agents include those of the cationic, anionic and non-ionic tape. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to for aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R_1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R_1$ is an inorganic or an organic cation, may be used in the formulation or the compounds of formula I wherein $R_1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3,-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4-dichlorophenoxy acetic acid (common name 2,4,-D) 2,4,5-trichlorophenoxyacetic acid (common name 2,4,5-T), 4-(4-chloro-2-methylphenoxy)butyric acid (common name MCPB), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dintrophenol (common name dinoterb), 2-secondarybutyl-4,6-dinitrophenol (common name dinoseb) and its ester dinoseb acetate;
E. dinitroaniline herbicides such as N', N'-diethyl2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);
H. 2-phenylpyridazin-3-ones such as 5-amino-4-chloro-2-phenylpyridazin-3-one (common name pyrazon);
I. uracil herbicides such as 3-cyclohexyl-5,6-trimethyleneuracil (common name lenacil), 5-bromo-3-secbutyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. Pyridine herbicides such as 3,6-dichloropicolinic acid (common name clopyralid) and 4-amino-3,5,6-trichloropicolinic acid (common name picloram);

M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl- α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189);

T. Aryloxyphenoxypropionate herbicides such as butyl 2-[4-(5-trifluoromethyl-2-pyridyloxy)phenoxy]propionate (common name fluazifop) and methyl 2-[4-(2,4-dichlorophenoxy)phenoxy]propionate (common name diclofop); and U. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

V. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

W. organoarsenical herbicides such as monosodium methanearsonate (common name MSMA); and X. amino acid herbicides such as N-(phosphonomethyl)glycine (common name glyphosate) and its salts and esters.

The invention is now illustrated by, but in no way limited to, the following Examples.

EXAMPLE 1

2-[1-(Ethoxyimino)propyl]-1,3-dioxa-1,2,3,4,4a,9,10,-10a-octahydrophenanthrene (1)

(i) Diethyl malonate (0.69 g; 4.3 mmole) was added to a solution of sodium metal (0.11 g; 4.7 mmole) in absolute ethanol (30 ml) and the mixture was heated under reflux for a period of 15 minutes. A solution of 2-acetyl-3,4-dihydronaphthalene (0.72 g; 4.3 mmole; Chemical Abstracts, 40, 6069 (1946)) in absolute ethanol 10 ml was added and the reaction mixture was heated under reflux for a further period of 6 hours. The ethanol was removed from the reaction mixture by distillation under reduced pressure and aqueous 10% sodium hydroxide solution (10) ml and toluene were added to the residue. The mixture was heated under reflux for a further 3 hours and then the aqueous layer was separated and added dropwise to a stirred aqueous solution of 5 N hydrochloric acid (100 ml) maintained at approximately 60° C. After stirring for a further 30 minutes the aqueous mixture was extracted with ethyl acetate (2×50 ml), the organic phase was dried over anhydrous sodium sulfate, and the solvent was removed by distillation under reduced pressure to give 1,3-dioxa-1,2,3,4,4a,9,10,10a-octahydrophenanthrene as an oil (0.33 g).

(ii) A mixture of 1,3-dioxa-1,2,3,4,4a,9,10,10a-octahydrophenanthrene (0.33 g; 1.5 mmole), zinc chloride (0.32 g; 2.3 mmole), propionic anydride (0.30 g; 2.3 mmole) and xylene (50 ml) was heated under reflux for a period of 1.5 hour. The reaction mixture was extracted with aqueous 5% sodium hydroxide solution (50 ml) and the aqueous extract was separated, acidified with concentrated hydrochloric acid and extracted with dichloromethane (50 ml). The organic phase was separated, dried over anhydrous sodium sulfate. The solution was concentrated and the product was purified by chromatography over silica gel (eluent dichloromethane) to give 2-propionyl-1,3-dioxa-1,2,3,4,4a,9,10,-10a-octahydrophenanthrene (80 mg). The product was characterized by proton nuclear magnetic resonance spectroscopy. Pmr (δ in ppm; CDCl$_3$): 1.20 (3H,t); 1.80–3.50 (10H,m); 7.30 (4H,s); 18.20 (1H,broad).

(iii) To a mixture of 2-propionyl-1,3-dioxa-1,2,3,4,4a,9,10,10a-octahydrophenanthrene (80 mg; 0.3 mmole) and ethoxyamine hydrochloride (60 mg; 0.6 mmole) in ethanol (50 ml) was added an aqueous 1% sodium hydroxide solution (2 ml). The mixture was stirred at room temperature for a period of 4 hours and then the solvent was removed by distillation under reduced pressure. The residue was dissolved in dichloromethane and the product was purified by chromatography over silica gel (eluant dichloromethane) to give 2-[1-(ethoxyimino)propyl]-1,3-dioxa-1,2,3,4,4a,9,10,10a-octahydrophenanthrene (37 mg) as a pale yellow oil.

The product was characterized by proton nuclear magnetic resonance spectroscopy, and the data are recorded in Table 2, Example 23.

EXAMPLE 2

Cis- and trans-
2-[1-(Ethoxyimino)propyl]-6-methyl-1,3-dioxa-
1,2,3,4,4a,9,10,10a-octahydrophenanthrene (7) and (i) 7-Methyl-3,4-dihydronaphthalene was converted into 2-acetyl-7-methyl-3,4-dihydronaphthalene using the general method outlined by Doyle et al (*Tetrahedron Letters,* 1973, 2903).

(ii) 6-Methyl-1,3-dioxa-1,2,3,4,4a,9,10,10a-octahydrophenanthrene was prepared from 2-acetyl-7-methyl-3,4-dihydronaphthalene following essentially the same procedure as that given in Example 1 part (i) and the compound was isolated as a colourless solid mp 205° C.

(iii) Propionyl chloride (0.42 ml) was added to a solution of 6-methyl-1,3-dioxa-1,2,3,4,4a,9,10,-10a-octahydrophenanthrene (1.0 g) and pyridine (0.39 ml) in dichloromethane (20 ml) with stirring at 20° C. The solution was kept at 20° C for 0.5 hours then washed with dilute hydrochloric acid (1 M, 20 ml), separated and dried over magnesium sulphate. The solvent was removed under reduced pressure and the residue was dissolved in toluene (30 ml) and heated under reflux at 90° C. 4-Dimethylaminopyridine (0.03 g) was added to the solution and heating was continued for 6 hours. The reaction mixture was concentrated under reduced pressure and the crude product was chromatographed on silica gel using dichloromethane as eluent. The first product eluted was 6-methyl-2-propionyl-1,3-dioxa-1,2,3,4,4a, 9,10,10a-octahydrophenanthrene (200 mg), isolated as a colourless solid, mp 92° C. The proton nuclear magnetic resonance spectrum of the product [CDCl$_3$; δ in ppm]: 1.16 (3H,t); 1.2 (2H,m); 2.30 (3H,s); 2.0–3.5 (8H,m); 6.98 (3H,bs); 18.08 (0.7H,s); 18.67 (0.3H,s) indicated that it was a single geometrical isomer which has been assigned the structure with a cis-ring junction.

Later fractions gave a second geometrical isomer, which is tentatively assigned the structure with a trans-ring junction, (200 mg) as a colourless solid, mp 90–95° C. Proton nuclear magnetic resonance spectrum (CDCl$_3$; δ in ppm): 1.16 (3H, t); 1.9–3.5 (10H,m); 2.27 (3H,s); 6.94 (3H,bs); 18.03 (0.4H,s); 18.12 (0.6H,s).

(iv) The two isomers of 6-methyl-2-propionyl-1,3-dioxa-1,2,3,4,4a,9,10,10a-octahydrophenanthrene were separately reacted with ethoxyamine hydrochloride following essentially the same procedure as described in Example 1 part (iii). The resultant isomers of 2-[1-(ethoxyimino)propyl]-6-methyl-1,3-dioxa-1,2,3,4,4a,9,10,10a-octahydrophenanthrene (7) and (8) were primarily characterized by their proton nuclear magnetic resonance spectra and for convenience the spectroscopic data is recorded in Example 23 Table 2.

EXAMPLE 3

Compounds Nos 2, 3, 4, 5, 6, 9, 12 and 13 were prepared starting from the appropriate 3,4-dihydronaphthalene and following essentially the same sequence as described for compounds 7 and 8 in Example 2 parts (i) to (iv).

Compounds Nos 28 and 34 were prepared in an entirely analogous manner commencing with indene and benzosuberone respectively and following essentially the same procedure as that described in Example 2 parts (i) to (iv).

Each of the products was characterized by proton nuclear magnetic resonance spectroscopy and the spectroscopic data is reported in Table 2, Example 23.

EXAMPLE 4

2-[1-(Ethoxyimino)propyl]-6-(1-hydroxyethyl)-1,3-dioxa-1,2,3,4,4a,9,10,10a-octahydrophenanthrene (10)

(i) 6-acetyl-1,3-dioxa-1,2,3,4,4a,9,10,10a-octahydrophenanthrene was prepared from 2,7-diacetyl3,4-dihydronaphthalene (JCS, 2110, 1953) following essentially the same procedure as that described in Example 1 part (i).

(ii) To a solution of 6-acetyl-1,3-dioxa-1,2,3,4,4a,9,10,10a-octahydrophenanthrene (3.95 g) in dimethylformamide (130 ml) was added sodium hydride (0.36 g) with stirring. The mixture was heated to 110° C. and propionic anhydride (2.0 g) was added. After 0.5 hours at 110° C. the mixture was cooled, poured into dilute hydrochloric acid (200 ml, 5%) and extracted with dichloromethane. The organic layer was dried over magnesium sulphate and evaporated to give a yellow paste (2.3 g). Purification by column chromatography on silica gel (eluant dichloromethane) gave 6-acetyl-2-propionyl-1,3-dioxa-1,2,3,4,4a,9,10,10a-octahydrophenanthrene as an oil (1.2 g) which was characterized by its proton nuclear magnetic resonance spectrum (CDCl$_3$; δ in ppm): 1.16 (3H,t); 1.6–3.7 (10H,m); 2.58 (3H,s); 7.0–7.9 (3H,m); 18.04–18.70 (1H,4xs).

(iii) A solution of 6-acetyl-2-propionyl-1,3-dioxa-1,2,3,4,4a,9,10,10a-octahydrophenanthrene (0.78 g) and sodium (0.06 g) in ethanol (50 ml) was stirred while sodium borohydride (0.15 g) was added portionwise over a period of 0.5 hour. Stirring was continued at room temperature for a further 0.5 hour and then the mixture was quenched with water, followed by dilute hydrochloric acid. The aqueous mixture was extracted with dichloromethane (2×100 ml) and the dichloromethane layer was dried and evaporated to give a yellow oil (0.98 g). Purification by column chromatography gave 6-(1-hydroxyethyl)-2-propionyl-1,3-dioxa-1,2,3,4,4a,9,10,10a-octahydrophenanthrene (0.20 g) as a colourless oil. Proton magnetic resonance spectrum (CDCl$_3$; δ in ppm): 1.14 (3H,t); 1.46 (3H,d); 1.6–3.5 (10H,m); 4.87 (10H,q); 7.1 (3H,bs); 18.10 and 18.18 (1H,2xs).

(iv) Reaction of 6-(1-hydroxyethyl)-2-propionyl-1,3-dioxa-1,2,3,4,4a,9,10,10a-octahydrophenanthrene with ethoxyamine hydrochloride following essentially the same procedure as that described in Example 1 part (iii) gave 2-[1-(ethoxyimino)propyl]-6-(1-hydroxyethyl)-1,3-dioxa-1,2,3,4,4a,9,10,10a-octahydrophenanthrene (10) as a colourless oil. The compound was characterized by its proton resonance magnetic spectrum (CDCl$_3$; δ in ppm): 1.15 (3H,t); 1.24 (3H,t); 1.48 (3H,d); 1.5–3.5 (lOH,m); 4.12 (2H,q); 4.84 (lH,q); 7.1 (3H,bs); 15.2 (lH,brs).

EXAMPLE 5

2-[1-(Ethoxyimino)propyl]-6-acetyl-1,3-dioxa-
1,2,3,4,a,9,10,10a - octahydrophenanthrene (11)

To a solution of 2-[1-(ethoxyimino)propyl]-6-(1hydroxyethyl)-1,3-dioxa-1,2,3,4,4a,9,10,10a-octahydrophenanthrene (10) (0.66 g) in methylene chloride (40 ml) was added, with stirring at 20° C., pyridinium chlorochromate (0.44 g). The mixture was stirred at 20° C. for 10 minutes then chromatographed on a column of silica gel (eluant dichloromethane) to give 2-[1-(ethoxyimino)propyl]-6-acetyl-1,3-dioxa-1,2,3,4,4a,9,10,10a-octahydrophenanthrene (11) as a brown oil. The compound was characterized by its proton nuclear magnetic resonance spectrum (CDCl$_3$; δ in ppm): 1.16 (3H,t); 1.24 (3H,t); 1.16–3.7 (10H,m); 2.56 (3H,s); 4.14 (2H,q); 7.0–7.9 (3H,m); 15.0 (1H,brs).

EXAMPLE 6

2-[1-(Ethoxyimino)propyl]-5,6,7,8-tetramethyl-1,3-dioxa-1,2,3,4,4a,9,10,10a - octahydrophenanthrene (14)

(i) To a stirred solution of ethyl 4-(2,3,4,5-tetramethylphenyl)butyrate (6.0 g) in dichloromethane (100 ml) at 0° C. was added titanium tetrachloride (5.3 m) over a period of 15 minutes. A solution of 1,1-dichloromethyl methyl ether (2.2 ml) in dichloromethane (10 ml) was then added dropwise as the stirring was continued and the temperature maintained at 0–5° C. The solution was stirred for 1 hour at 5° C. and then for 3 hours at 15° C. and was then poured into ice water. The two-phase mixture was shaken thoroughly and the organic layer was separated, dried (MgSO$_4$) and evaporated to give ethyl 4-(2-formyl-3,4,5,6-tetramethylphenyl)butyrate (6 g) as a pale brown oil. Proton magnetic resonance spectrum (CDCl$_3$; δ in ppm): 1.26 (3H, t); 1.6–2.0 (2H, m); 2.1–2.5 (14H,m); 2.6–3.0 (2H,m); 4.11 (2H,q); 10.56 (1H,s).

(ii) A solution of ethyl 4-(2-formyl-3,4,5,6-tetramethylphenyl)butyrate (5 g) and 1-triphenylphosphoranylidene-2-propanone (6 g) in toluene (100 ml) was boiled under reflux for 24 hours. The toluene was removed by evaporation under reduced pressure and the residue was purified by column chromatography on silica gel (eluant chloroform) to give ethyl 4-[2-(3-oxo-1-butenyl)-3,4,5,6-tetramethylphenyl]butyrate (5 g) as a pale brown oil. Proton nuclear magnetic resonance spectrum (CDCl$_3$; δ in ppm): 1.24 (3H,t); 1.6–2.0 (2H,m); 2.1–2.4 (14H,m); 2.40 (3H,s); 2.5–2.8 (2H,m); 4.11 (2H,q); 6.12 (1H,d); 7.71 (1H,d).

(iii) Sodium methoxide (0.6 g) was added to boiling xylene (40 ml) and the suspension was stirred vigorously as a few millilitres of xylene were distilled from the flask. Dimethylsulphoxide (0.5 ml) was added to the suspension followed by ethyl 4-[2-(3-oxo-1-butenyl)-3,4,5,6-tetramethylphenyl]butyrate (3.2 g) and potassium t-butoxide (1.2 g). A vigorous reaction took place and a small volume of alcohol distilled from the reaction flask. Heating was continued for a further hour and another 10 ml of xylene was collected by distillation. The suspension was then cooled, poured into dilute hydrochloric acid and ethylacetate (100 ml) was added. The organic layer was separated, dried (MgSO$_4$) and the solvents evaporated under reduced pressure. The crude product was purified by column chromatography on silica gel (eluant chloroform/ methanol) to give 5,6,7,8-tetramethyl-1,3-dioxa1,2,3,4,4a,9,10,10a-octahydrophenanthrene (0.8 g) as a colourless solid. Proton magnetic resonance spectrum (CDCl$_3$; δ in ppm); 2.1–2.2 (12H,bs); 2.3–3.0 (7H,m); 3.6 (1H,m); 5.6 (1H,s); 6.8 (1H,bs).

(iv) Propionic anhydride (0.4 ml) was added to a stirred suspension of 5,6,7,8-tetramethyl-1,3 dioxa-1,2,3,4,4a,9,10,10a-octahydrophenanthrene (0.7 g) in toluene (60 ml). The mixture was heated at 110° C. for 0.5 hour during which a homogeneous solution was formed. 4-Dimethylaminopyridine (0.10 g) was added and the solution was heated under reflux for a total of 8 hours at 110° C. The solution was washed with dilute hydrochloric acid and then the organic layer was dried (MgSO$_4$) and evaporated under reduced pressure. The crude product was purified by column chromatography on silica gel (eluant chloroform) to give 2-propionyl-5,6,7,8-tetramethyl-1,3-dioxa-1,2,3,4,4a,9,10,10a-octahydrophenanthrene (600 mg) as a colourless solid. Proton magnetic resonance spectrum (CDCl$_3$; δ in ppm): 1.16 (3H,t); 1.9–3.2 (21H,m); 3.4–3.8 (1H,m); 18.05 (0.5H,s); 18.11 (0.5H,s).

(v) Reaction of 2-propionyl-5,6,7,8-tetramethyl-1,3-dioxa-1,2,3,4,4a, 9,10,10a-octahydrophenanthrene with ethoxyamine hydrochloride following essentially the same procedure as that described in Example 1, part (iii) gave 2-[1-(ethoxyimino)propyl]-5,6,7,8-tetramethyl-1,3-dioxa-1,2,3,4,4a,9,10,10a-octahydrophenanthrene (14) as a low-melting point crystalline solid. The compound was characterized by its proton magnetic resonance spectrum and the data are recorded in Table 2, Example 23.

EXAMPLE 7

Compounds Nos 15, 16, 17, 18, 19 and 20 were prepared starting from the appropriate 4-(substituted phenyl) butyric acid ester and following essentially the same procedure as described for compound 14 in Example 6 parts (i) to (v).

Each of the necessary starting 4-(substituted phenyl) butyric acid esters was prepared by standard literature methods and the final products were characterized by proton magnetic resonance spectroscopy and the spectroscopic data is reported in Table 2, Example 23.

EXAMPLE 8

6,8-Dimethyl-7-N,N-dimethylsulfamoyl -2-[1-(ethoxyimino)propyl]-1,3-dioxa-1,2,3,4,4a,9,10,10a -octahydrophenanthrene (21)

(i) To an ice cooled solution of 6,8-dimethyl-2-propionyl-1,3-dioxa-1,2,3,4,4a,9,10,10a-octahydrophenanthrene (0.70 g) in chloroform (20 ml), chlorosulfonic acid (1.3 ml) was added dropwise with stirring. The mixture was stirred for 3 hours at 0°–5° C. then poured onto ice. The organic layer was separated and then treated with stirring with excess of an aqueous solution of dimethylamine (5 ml, 20%). The two phase reaction mixture was stirred for 3 hours at room temperature and then acidified with dilute hydrochloric acid. The chloroform layer was separated, dried (Mg SO4) and evaporated to give 6,8-dimethyl-7-N,N-dimethylsulfamoyl-2-propionyl-1,3-dioxa-1,2,3,4,4a,9,10,10 a-octahydrophenanthrene (0.70 g, 73%) as a low-melting point solid.

(ii) A mixture of 6,8-dimethyl-7-N,N-dimethyl-sulfamoyl-2-propionyl-1,3-dioxa-1,2,3,4,4a,9,10,10a-octahydrophenanthrene (0.70 g), ethoxyamine hydrochloride (0.25 g) and sodium acetate (0.25 g) was stirred in ethanol (30 ml) for 18 hours. The ethanol was removed under reduced pressure and the residue was partitioned between water and chloroform. The chloroform layer was dried (MgSO)4) and evaporated to give 6,8-dimethyl-7-N,N-dimethylsulfamoyl-2- [1-ethoxyimino)propyl]-1,3-dioxa-1,2,3,4,4a,9,10, 10a-octahydrophenanthrene (21) as a brown oil (600 mg). The compound was characterized by its proton magnetic resonance spectrum which is recorded in Table 2, Example 23.

EXAMPLE 9

2-[1-(Ethoxyimino)propyl]-6-methoxy-5,7-dimethyl-8-nitro
-1,3-dioxa-1,2,3,4,4a,9,10,10a-octahydrophenanthrene
(22)

(i) A mixture of fuming nitric acid (0.5 g), acetic anhydride (0.5 g) and acetic acid (0.5 g) was added dropwise with stirring to an ice-cooled solution of 6-methoxy-5,7-dimethyl-2-propionyl-1,3-dioxa-1,2,3,4,4a, 9,10,10a-octahydrophenanthrene (1.5 g) in acetic anhydride (3 ml). The mixture was stirred at room temperature (20° C.) for 12 hours and then poured into water and extracted with diethyl ether. The ether layer was dried and evaporated and the crude product was chromatographed on silica, eluting with dichloromethane. Pure 6-methoxy-5,7-dimethyl -8-nitro-2-propionyl-1,3-dioxa-1,2,3,4,4a,9,10,10a-octahydrophenanthrene was obtained as a pale yellow oil (0.2 g, 12%).

(ii) The trione from part (1) was reacted with ethoxyamine following essentially the same procedure as described in Example 8, part (ii). 2-[1-(ethoxyimino)-propyl]-6-methoxy-5,7-dimethyl8-nitro-1,3-dioxa-1,2,3,4,4a,9,10,10a-octahydrophenanthrene (22) was obtained as a pale yellow oil which was characterized by its proton magnetic resonance spectrum which is recorded in Table 2, Example 23.

EXAMPLE 10

7-Acetyl-6,8-dimethyl-2-[1-(ethoxyimino)propyl]-1,3
-dioxa - 1,2,3,4,4a,9,10,10a-octahydrophenanthrene (23)

(1) A mixture of aluminum trichloride (1.5 g, 11 m mole) and 6,8-dimethyl-2-propionyl-1,3-dioxa-1,2,3,4,4a,9,10,10a-octahydrophenanthrene (1.0 g, 3.3 m mole) in dichloroethane (20 ml) was cooled to 0°–5° C. and stirred for 0.5 hours. Acetyl chloride (0.7 ml, 10 m mole) was added and stirring was continued as the solution was allowed to come to room temperature. After 15 hours the solution was poured into dilute hydrochloric acid and the whole was stirred and heated until all the dichloroethane had evaporated. The crude product was extracted into chloroform and the chloroform layer was dried (Mg SO4) evaporated and chromatographed over silica, eluting with chloroform. 7-Acetyl-6,8-dimethyl-2-propionyl-1,3-dioxa-1,2,3,4,4a,9,10,10a-octahydrophenanthrene was obtained as a colourless oil, proton magnetic resonance spectrum (CDCl$_3$; δ in ppm): 1.18(3H,t); 2.08(3H,s); 2.18(3H,s); 2.42(3H,s); 2.0–3.6 (10H,m); 6.81(0.5H,s); 6.95(0.5H,s); 18.1(1H, broad).

(ii) The trione from part (i) was reacted with ethoxyamine following the same procedure as given in Example 8, part (ii). 7-Acetyl-6,8-dimethyl-2-[1-(ethoxyimino)-propyl]-1,3-dioxa-1,2,3,4,4a,9,10,10a-octahydrophenanthrene (23) was obtained as a pale brown oil which was characterized by its proton magnetic resonance spectrum which is recorded in Table 2, Example 23.

EXAMPLE 11

8-Acetyl-5,6,7-trimethyl-2-[1-(ethoxyimino) propyl]-1,3-dioxa-1,2,3,4,4a,9,10,10a-octahydrophenanthrene (24) was prepared from 5,6,7-trimethyl-2-propionyl-1,3-dioxa-1,2,3,4,4a,9,10,10a-octahydrophenanthrene following essentially the same procedure as given in Example 10, parts (i) and (ii). The product was characterized by its proton magnetic resonance spectrum which is recorded in Table 2, Example 23.

EXAMPLE 12

Compounds Nos 25 and 26 were prepared by reaction of the appropriate alkoxyamine with the appropriate 2-propionyl-1,3-dioxa-1,2,3,4,4a,9,10,10a -octahydrophenanthrene according to the procedure given in Example 8, part (ii). The compounds were characterized by their proton magnetic resonance spectra which are recorded in Table 2, Example 23.

EXAMPLE 13

Sodium salt of
2-[1-(ethoxyimino)butyl]-1,3-dioxa-1,2,3,4,4a,9,10,10a-octahydrophenanthrene (27)

A solution of sodium hydroxide (0.75 ml of a 2% solution) was added to a solution of 2-[1-(ethoxyimino)-butyl]-1,3-dioxa-1,2,3,4,4a,9,10,10a-octahydrophenanthrene (1) (0.12 g) in ethanol (3 ml) at room temperature. The solution was evaporated under reduced pressure and the residue was azeotroped with toluene to remove all the water. The sodium salt (27) (135 mg) was obtained as a pale brown noncrystalline solid, mp>200° (dec).

EXAMPLE 14

5,7-Dimethyl-2-[1-(ethoxyimino)propyl]-1,3-dioxa-1,2,3,4,4a,9a-hexahydrofluorene (29)

(i) Reaction of methyl 3-(3,5-dimethylphenyl) propionate with dichloromethyl methyl ether according to the method given in Example 6, part (i) gave a mixture of methyl 3-(3,5-dimethyl-4-formyl phenyl) propionate and methyl 3-(3,5-dimethyl-2-formyl phenyl) propionate. Treatment of this mixture of aldehydes with 1-triphenylphosphor anylidene-2-propanone following the conditions described in Example 6, part (ii) gave a mixture of methyl 3-[3,5-dimethyl-4-(3-oxo-1-butenyl)phenyl] propionate and methyl 3-[3,5-dimethyl-2-(3-oxo-1-butenyl) phenyl] propionate.

(ii) The mixture of isomeric butenones from part (ii) (4.3 g, 16.5 m mole) in xylene (30 ml) was added to a stirred suspension of potassium tertiary butoxide (1.86 g, 16.5 m mole) in boiling xylene (70 ml). The mixture was stirred and refluxed for 0.75 hours and then poured into dilute aqueous sodium hydroxide. The aqueous layer was separated, acidified and extracted with ethyl acetate. The organic layer was dried (MgSO4) and evaporated to give 5,7-dimethyl-1,3-dioxa-1,2,3,4,4a,9a-hexahydrofluorene as a brown glassy solid (2.9 g).

(iii) Reaction of 5,7-dimethyl-1,3-dioxa-1,2,3,4,4a, 9a-hexahydrofluorene following the procedure given in Example 6, parts (iv) and (v) gave 5,7-dimethyl-2-[1-(ethoxyimino)propyl]-1,3-dioxa-1,2,3,4,4a,9a -hexahydrofluorene (29) as a brown oil. The compound was characterized by its proton magnetic resonance spectrum and the data are recorded in Table 2, Example 23.

EXAMPLE 15

Compounds Nos 30, 31, 32 and 33 were prepared following the same method as described in Example 14 and starting with the appropriate 3-(substituted phenyl) propionic acid ester and using the appropriate alkoxyamine in the final stage. The compounds were characterized in part by their proton magnetic resonance spectra and the data are recorded in Table 2, Example 23.

EXAMPLE 16

[1-(Ethoxyimino)propyl]-10,10a-dihydro-6H-dibenzo[b,d]-pyran-6,7,9-(6aH,8H)trione (35)

(i) A mixture of benzylchloride (8.8 g), 4-(2-hydroxy phenyl)-but-3-en-2-one (11.4 g) and anhydrous potassium carbonate (11.0 g) in methyl ethyl ketone (100 ml) was stirred and heated under reflux for 5 hours. The mixture was poured into water (300 ml) and extracted with chloroform (200 ml). The chloroform extracts were washed with dilute sodium hydroxide solution and then dried over magnesium sulphate and evaporated to give 4-(2-benzyloxyphenyl)-but-3-en-2-one (15 g) as a pale yellow oil.

(ii) To a solution of sodium metal (1.5 g) in absolute ethanol (100 ml) was added diethylmalonate (10.5 g) and the solution was stirred and heated to boiling. 4-(2-Benzyloxyphenyl)but-3-en-2-one (15 g) was added to the solution and stirring and heating were continued for 3 hours. The mixture was cooled and neutralized with dilute hydrochloric acid and then extracted with chloroform (200 ml). The chloroform extracts were dried (MgSO$_4$) and evaporated to give 5-(2-benzyloxy)phenyl-4-ethoxycarbonylcyclohexane-1,3-dione as a low-melting point solid.

(iii) Reaction of 5-(2-benzyloxy)phenyl-4-ethoxycarbonylcyclohexane-1,3-dione with propionyl chloride following essentially the same procedure as that described in Example 2, part (iii) gave 5-(2-benzyloxy)-phenyl-4-ethoxycarbonyl-2-propionylcyclohexane-1,3-dione as a pale yellow oil, proton magnetic resonance spectrum (CDCl$_3$; δ in ppm): 0.8–1.3 (6H,m); 2.8–4.3 (8H,m); 5.10 (2H,s); 6.8–7.4 (9H,m); 18.13 and 18.22 (1H,2xs).

(iv) To a solution of 5-(2-benzyloxy)phenyl-4-ethoxycarbonyl-2-propionylcyclohexane-1,3-dione (2.1 g) in ethyl acetate (100 ml) was added 10% palladium on charcoal (380 mg) and the suspension was stirred vigorously at room temperature under a hydrogen atmosphere for 2.5 hours. The catalyst was removed by filtration and the filtrate was concentrated under reduced pressure to give 5-(2-hydroxyphenyl)-4-ethoxycarbonyl-2-propionylcyclohexane-1,3-dione as a pale yellow oil, proton magnetic resonance spectrum (CDCl$_3$; δ in ppm): 0.8–1.3 (6H,m); 2.8–4.3 (8H,m); 6.6–7.2 (4H,m); 18.2 (1H,bs); phenolic OH not observed.

(v) A solution of 5-(2-hydroxyphenyl)-4-ethoxycarbonyl-2-propionylcyclohexane-1,3-dione (100 mg) and p-toluenesulphonic acid (10 mg) in toluene (5 ml) was heated under reflux for 1 hour. The solution was washed with dilute aqueous sodium bicarbonate and the toluene layer was dried (MgSO$_4$) and evaporated to give 8-propionyl-10,10a-dihydro-6H-dibenzo[b,d]-pyran-6,7,9-(6aH,8H)trione (80 mg) as a pale yellow oil, proton magnetic resonance spectrum (CDCl$_3$; δ in ppm): 0.8–1.3 (3H,m); 2.8–4.0 (6H,m); 6.9 (4H,bs); 18.1 (1H,bs).

(vi) Reaction of 8-propionyl-10,10a-dihydro-6H-dibenzo[b,d]pyran-6,7,9-(6aH,8H)trione with ethoxyamine hydrochloride following essentially the same procedure as that described in Example 8 part (ii) gave 8-[1-(ethoxyimino)propyl]-10,10a-dihydro-6H,dibenzo[b,d]pyran-6,7,9-(6aH,8H)trione (35) as a yellow oil. The compound was characterized by its proton magnetic resonance spectrum and the data are recorded in Table 2, Example 23.

EXAMPLE 17

[1-(Ethoxyimino)propyl]-10a-ethoxycarbonyl-7-methyl-1,3,9-trioxa-1,2,3,4,4a,9,10,10a-octahydrophenanthrene (36)

(i) Ethyl 4-benzyloxy-1-ethoxycarbonyl-6-(4-methylphenyl-2-oxo-cyclohex-3-enylacetate was prepared from ethyl 6-(4-methylphenyl)cyclohexane-2,4-dione carboxylate following the general method described in British Pat. No. 1,416,705.

(ii) A solution of ethyl 4-benzyloxy-1-ethoxycarbonyl-6-(4-methylphenyl)-2-oxo-cyclohex-3-enyl acetate (2 g) and sodium hydroxide (0.44 g) in aqueous ethanol (50 ml, 1:1) was boiled for 4 hours. Acidification with dilute hydrochloric acid and extraction of the cooled aqueous suspension with ethyl acetate gave 4-benzyloxy-1-ethoxycarbonyl-6-(4-methylphenyl)-2-oxo-cyclohex-3-enylacetic acid as a white solid, mp 217° C.

(iii) A suspension of 4-benzyloxy-1-ethoxycarbonyl-6-(4-methylphenyl)-2-oxo-cyclohex-3-enylacetic acid (6.7 g) in sulphuric acid (80%, 100 ml) was heated at 60° C. for 8 hours and then poured into water (300 ml) and extracted with ethyl acetate. The ethyl acetate layer was dried and evaporated to give 10a-ethoxycarbonyl-7-methyl-1,3,9-trioxa-1,2,3,4,4a,9,10,10a-octahydrophenanthrene (5.1 g) as a cream solid, mp 160° C.

(iv) Pyridine (0.4 ml) was added at room temperature to a stirred solution of 10a-ethoxycarbonyl-7-methyl-1,3,9-trioxa-1,2,3,4,4a,9,10,10a-octahydrophenanthrene (1.0 g) in methylene chloride (20 ml). Propionyl chloride (0.42 ml) was added to the solution and stirring was continued for 20 minutes before the mixture was washed with dilute hydrochloric acid followed by water. The methylene chloride layer was separated, dried and evaporated and the residue was dissolved in toluene, heated to 100° C. and 4-dimethylaminopyridine (0.03 g) was added. After 3 hours at 100°–110° C. the toluene solution was washed with dilute hydrochloric acid and then extracted with dilute sodium hydroxide solution and the extracts acidified and extracted with dichloromethane. After drying, the methylene chloride layer was evaporated and the crude product was purified by column chromatography on silica gel (eluant dichloromethane) to give 10a-ethoxycarbonyl-7-methyl-2-propionyl-1,3,9-trioxa-1,2,3,4,4a,9,10,10a-octahydrophenanthrene (0.4 g) as a pale orange solid, mp 120° C.

(v) Sodium acetate (0.14 g) was added with stirring to a solution of ethoxyamine hydrochloride (0.17 g) and 10a-ethoxycarbonyl-7-methyl-2-propionyl-1,3,9-trioxa-1,2,3,4,4a,9,10,10a-octahydrophenanthrene (0.64 g) in ethanol (70 ml) at 20° C. After 24 hours the solvent was removed under reduced pressure and the residue was partitioned between methylene chloride and water. Evaporation of the dried methylene chloride layer gave 2-[1-(ethoxyimino)propyl)-10a-ethoxycarbonyl-7-methyl-1,3,9-trioxa-1,2,3,4,4a,9,10,10a-octahydrophenanthrene (36) as a brown oil (0.7 g).

The compound was characterized by proton nuclear resonance spectroscopy and the spectroscopic data is reported in Table 2, Example 23.

EXAMPLE 18

3-[1-(Ethoxyimino)propyl]-2,4-dioxa-1,2,3,4,4a,9b-hexahydrodibenzofuran (37)

(1) 2,4-Dioxa-1,2,3,4,4a,9b-hexahydrodibenzofuran was prepared following the method of Takahashi (Chemical Abstracts 1962: 15045i).

(ii) 2,4-Dioxa-1,2,3,4,4a,9b-hexahydrodibenzofuran was converted into 3-[1-(Ethoxyimino)propyl]-2,4-dioxa-1,2,3,4,4a,9b-hexahydrodibenzofuran (37) following essentially the same procedure as that described in Example 2 parts (iii) and (iv). The product was characterized by proton magnetic resonance spectroscopy and the spectroscopic data is reported in Table 2, Example 23.

EXAMPLE 19

Compound No 38 was prepared starting from 2,4-dimethyl -6-hydroxybenzaldehyde and following the same procedure as that described in Example 18 parts (i) and (ii). The product was characterized by proton magnetic resonance spectroscopy and the spectroscopic data is reported in Table 2, Example 23.

EXAMPLE 20

8-[1-(Ethoxyimino)propyl]-6a,7,8,9,10,10a-hexahydro-6H-dibenzo[b,d]pyran-7,9-dione (39)

(i) 3-Acetyl-2H-1-benzopyran was prepared according to the method of DeBoer (*J. Org. Chem.*, 39, 2426 (1974)).

(ii) Starting from 3-acetyl-2H-1-benzopyran and following essentially the same procedure as described in Example 2 part (ii) and then Example 6 parts (iv) and (v) gave 8-[1-(ethoxyimino)propyl]-6a,7,8,9,10,10a-hexahydro-6H-dibenzo[b,d]pyran-7,9-dione (39). The compound was characterized by proton magnetic resonance spectroscopy and the spectroscopic data is reported in Table 2, Example 23.

EXAMPLE 21

3-[1-(Ethoxyimino)propyl]-8,10-dimethyl-1,2,3,4,4a,10b-hexahydro-6H-dibenzo[b,d]thiopyran-2,4-dione (40)

(i) Ethyl (3,5-dimethylbenzyl)thioacetate was converted into an approximately 1:1 mixture of ethyl [2-(3-oxo-but-1-enyl)-3,5-dimethylbenzyl]thioacetate and ethyl [4-(3-oxo-but-1-enyl)-3,5-dimethylbenzyl]thioacetate following essentially the same procedure as that described in Example 6 parts (i) and (ii). The mixture was reacted under the conditions described in Example 6 part (iii) to give 8,10-dimethyl-1,2,3,4,4a,10b-hexahydro-6H-dibenzo[b,d]thiopyran-2,4-dione plus unreacted ethyl [4-(3-oxo-but-1-enyl)-3,5-dimethylbenzyl]thioacetate.

(ii) 8,10-Dimethyl-1,2,3,4,4a,10b-hexahydro-6H-dibenzo[b,d]thiopyran-2,4-dione was converted into 3-[1-(ethoxyimino)propyl]-8,10-dimethyl-2,3,4,4a,10b-hexahydro-6H-dibenzo[b,d]thiopyran-2,4-dione (40) following essentially the same procedure as that described in Example 6 parts (iv) and (v). The compound was characterized by its proton magnetic resonance spectrum and the data are recorded in Table 2 Example 23.

EXAMPLE 22

Compound No 41 was prepared starting from ethyl (2,3,4,5-tetramethyl benzyl) thioacetate and following the procedure outlined in Example 21, parts (i) and (ii). The compound was characterized by its proton magnetic resonance spectrum and the data are recorded in Table 2, Example 23.

EXAMPLE 23

The majority of the compounds of the invention were obtained as oils and were characterized by, and can be identified by, their nuclear magnetic resonance spectra. For convenience proton magnetic resonance (pmr) spectroscopic data is recorded in Table 2 below.

TABLE 2

| Compound No | Appearance | Proton Chemical Shift $\delta$ in ppm (CDCl$_3$) |
|---|---|---|
| 1 | pale yellow oil | 1.07.1.40(6H,m); 1.90–3.00 (9H,m); 3.40(1H,m); 4.12(2H,q); 7.14(4H,s); 14.90(1H,s). |
| 2 | pale yellow oil | 1.0–1.4(6H,m); 1.6–3.7(10H,m); 4.11(2H,q); 7.1(4H,bs); 14.8(1H,broad). |
| 3 | pale yellow oil | 1.0–1.4(6H,m); 1.7–3.6(10H,m); 4.10(2H,q); 7.1(4H,bs); 14.8(1H,broad) |
| 4 | pale yellow oil | 0.8–1.1(3H,m); 1.33(3H,t); 1.5–3.6(12H,m); 4.12(2H,q); 7.1(1H,bs); OH not observed |
| 5 | pale yellow solid | 0.99(3H,t); 1.31(3H,t); 1.4–3.45(12H,m); 4.10(2H,q); 7.1(4H,bs); 15.2(1H,broad) |
| 6 | pale yellow oil | 0.96(3H,t); 1.30(3H,t); 1.4–1.8(2H,m); 1.9–3.1(9H,m); 3.3–3.7(1H,m); 4.10(2H,q); 7.14(4H,s); 15.0(1H, broad) |
| 7 | brown oil | 1.0–1.5(6H,m); 2.28(3H,s); 2.1–3.5(10H,m); 4.08(2H,q); 7.0(3H,bs); 14.8(1H,broad) |
| 8 | brown oil | 1.0–1.4(6H,m); 2.28(3H,s); 2.0–3.6(10H,m); 4.09(2H,q); 6.95(3H,bs);d 14.8(1H,broad) |
| 9 | pale yellow oil | 1.0–1.4(6H,m); 2.27(3H,s); 2.0–3.5(10H,m); 4.08(2H,q); 6.8–7.1(3H,m); 14.9(1H, broad) |
| 10 | colourless oil | 1.15(3H,t); 1.24(3H,t); 1.48(3H,d); 1.5–3.5(10H,m); 4.12(2H,q); 4.84(1H,q); 7.1 (3H,bs); 15.2(1H,broad s). |
| 11 | brown oil | 1.16(3H,t); 1.24(3H,t); 1.6–3.7(10H,m); 2.56(3H,s); 4.14 (2H,q); 7:0–7.9(3H,m); 15.0 (1H,broad s). |
| 12 | pale yellow oil | 1.16(3H,t); 1.32(3H,t); 2.20 (6H,s); 2.1–3.6(10H,m); 4.12 (2H,q); 6.89(2H,s); 14.92 (1H,broad). |
| 13 | pale yellow oil | 1.0–1.5(6H,m); 2.20(3H,5); 2.28(3H,s); 2.2–3.5(10H,m); 4.12(2H,q); 6.7–6.95(2H,m); 15.0(1H,broad). |
| 14 | colourless oil | 1.16(3H,t); 1.32(3H,t); 2.18 (3H,s); 2.22(9H,s); 2.1–3.7 (10H,m); 4.12(2H,q); 15.0 (1H,broad). |
| 15 | pale yellow oil | 1.18(3H,t); 1.33(3H,t); 2.25 (6H,s); 2.4–3.7(10H,m); 3.68 (3H,s); 4.13(2H,q); 6.82(1H,s); 15.0(1H,bs). |
| 16 | pale yellow oil | 1.19(3H,t); 1.33(3H,t); 2.14 (3H,s); 2.24(3H,s); 2.27(3H,s); 2.2–3.7(10H,m); 3.66 (3H,s); 4.14(2H,q); 15.0(1H, broad). |
| 17 | pale yellow oil | 1.19(3H,t); 1.33(3H,t); 2.22 (9H,bs); 2.1–3.7(10H,m); 3.67 (3H,s); 4.13(2H,q); 15.0 (1H, broad). |
| 18 | pale yellow oil | 1.19(3H,t); 1.33(3H,t); 2.13 (3H,s); 2.23(3H,s); 2.1–3.1 (15H,m); 3.5(1H,m); 4.13(2H,q); 15.0(1H, broad). |

TABLE 2-continued

| Compound No | Appearance | Proton Chemical Shift δ in ppm (CDCl$_3$) |
|---|---|---|
| 19 | pale yellow oil | 1.18(3H,t); 1.33(3H,t); 2.25 (3H,s); 2.30(3H,s); 2.2–3.1 (9H,m); 3.6(1H,m); 4.12(2H,q); 6.83(2H,s); 14.9(1H, broad). |
| 20 | brown oil | 1.19(3H,t); 1.32(3H,t); 2.16 (3H,s); 2.24(6H,s); 2.1–3.1 (9H,m); 3.5(1H,m); 4.12(2H,q); 6.82(1H,s); 14.9(1H, broad). |
| 21 | brown semi-crystalline solid | 1.16(3H,t); 1.33(3H,t); 2.1–3.5 (16H,m); 2.76(6H,s); 4.13(2H,q); 6.89(0.3H,s); 7.02(0.7H,s); 14.9 (1H, broad). |
| 22 | pale yellow oil | 1.18(3H,s); 1.34(3H,t) 2.19 (3H,s); 2.31(3H,s); 2.1–3.2 (9H,m); 3.5(1H,m); 3.70(3H,s); 4.14(2H,q); 15.0(1H, broad). |
| 23 | pale brown oil | 1.18(3H,t); 1.33(3H,t); 2.09 (3H,s); 2.19(3H,s); 2.1–3.5 (10H,m); 2.44(3H,d); 4.13(2H,q); 6.81(0.5H,s); 6.95(0.5H,s); 15.0(1H, broad). |
| 24 | pale brown oil | 1.18(3H,t); 1.33(3H,t); 2.18 (6H,s); 2.25(3H,s); 2.1–3.1 (9H,m); 3.5(1H,m); 15.0(1H, broad). |
| 25 | pale brown oil | 1.18(3H,t); 2.1–3.1(10H,m); 2.18(12H,bs); 4.5(2H,d); 5.3 (2H,m); 6.0(1H,m); 15.0(1H, broad). |
| 26 | pale yellow oil | 1.16(3H,t); 2.19(3H,s); 2.27 (3H,s); 2.1–3.1(10H,m); 3.5 (1H,m); 6.80(1H,s); 15.0(1H, broad). |
| 27 | brown non-crystalline solid | not recorded. |
| 28 | brown oil | 1.08(3H,t); 1.30(3H,t); 2.1–3.7(8H,m); 4.08(2H,q); 7.20 (4H,s); 15.0(1H, broad). |
| 29 | brown oil | 1.17(3H,t); 1.33(3H,t); 2.29 (6H,s); 2.2–3.8(8H,m); 4.13 (2H,q); 6.83(1H,s); 6.92(1H,s); 14.9(1H,bs). |
| 30 | pale yellow solid | 0.99(3H,t); 1.33(3H,t); 1.5 (2H,m); 2.19(12H,s); 2.1–3.8 (8H,m); 4.12(2H,q); 15.0(1H, broad); |
| 31 | colourless solid | 1.18(3H,t); 1.33(3H,t); 2.18 (12H,s); 2.2–3.8(8H,m); 4.12 (2H,q); 14.9(1H, broad). |
| 32 | pale yellow oil | 1.18(3H,t); 1.33(3H,t); 2.26 (6H,s); 2.2–3.8(8H,m); 3.70 (3H,s); 4.12(2H,q); 6.72(1H,s); 15.0(1H, broad). |
| 33 | colourless solid | 1.18(3H,t); 2.20(12H,s); 2.2–3.7(8H,m); 4.4(2H,m); 4.56(2H, dxt); 14.0(1H, broad). |
| 34 | brown oil | 0.96(3H,t); 1.31(3H,t); 1.3–3.7(12H,m); 4.10(2H,q); 7.1 (4H,bs); 15.0(1H, broad). |
| 35 | yellow oil | 1.10(3H,t);1.34(3H,t); 2.5–4.2(8H,m); 6.7–7.2(4H,m); 15.0(1H, broad). |
| 36 | brown oil | 0.94(3H,t); 1.18(3H,t); 1.35 (3H,t); 2.38(3H,s); 2.4–3.7 (7H,m); 3.92(2H,q); 4.15(2H, q); 7.1–7.4(3H,m); 7.89 (1H,s); 15.0(1H, broad). |
| 37 | pale orange oil | 0.9–1.4(6H,m); 2.4–3.0(4H, m); 3.8–4.2(3H,m); 5.0–5.3 (1H,m); 6.6–7.1(4H,m); OH not observed. |
| 38 | pale orange solid | 1.16(3H,t); 1.34(3H,t); 2.27 (3H,s); 2.4–3.1(4H,m); 3.6–4.0(1H,m); 4.14(2H,q); 5.0 (1H,bd); 6.55(2H,s); 15.0 (1H, broad). |
| 39 | orange oil | 1.0–1.5(6H,m); 2.0–4.9(10H, m); 6.7–7.1(4H,m); 15.0(1H, broad). |
| 40 | orange oil | 1.0–1.4(6H,m); 2.25(3H,s); 2.29(3H,s); 2.3–4.3(10H,m); 6.8(1H,s); 6.91(1H,s); OH not observed. |
| 41 | brown oil | 1.0–1.4(6H,m); 2.17(12H,bs); 2.1–3.1(4H,m); 4.1(6H,m);15.0 (1H, broad). |

EXAMPLE 24

This non-limiting Example illustrates the preparation of formulations of the compounds of the invention.

(a) Emulsifiable Concentrate

Compound No 13 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 27 (5 parts by weight and "Dyapol" PT (1 part by weight) were added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade mark and "Dyapol" PT is an anionic suspending agent; "Teric" N8 is a product of ethoxylation of nonylphenol.)

(c) Emulsifiable Concentrate

Compound No 13 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 13 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "aerosol" OT/B is a formulation of the dioctyl ester of sodium sulfosuccinic acid.)

(e) High Strength Concentrate

Compound No 13 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 13 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 25 and 26 and 27, in the evaluation of the pre-emergence and post-emergence herbicidal activity of the compounds.

EXAMPLE 25

The pre-emergent herbicidal activity of the compounds of the invention formulated as described in Example 24 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Or: Wild Oats
Rg: Ryegrass
Jm: Japanese millet
P: Peas
Ip: Ipomea
Ms: Mustard
Sf: Sunflower

TABLE 3

| Compound No | Application Rate (kg/ha) | Wh | Ot | Rg | Jm | P | Ip | Ms | Sf |
|---|---|---|---|---|---|---|---|---|---|
| 1 | 1.0 | 0 | 2 | 5 | 5 | 0 | 0 | 0 | 0 |
| 3 | 1.0 | 0 | 4 | 5 | 5 | 0 | 0 | 0 | 0 |
| 4 | 0.25 | 2 | 3 | 3 | 5 | — | — | — | — |
| 4 | 1.0 | 2 | 4 | 5 | 5 | 0 | 0 | 0 | 0 |
| 6 | 0.25 | 0 | 4 | 5 | 5 | 0 | 0 | 0 | 0 |
| 6 | 1.0 | 2 | 4 | 5 | 5 | 0 | 0 | 0 | 0 |
| 9 | 1.0 | 0 | 5 | 5 | 5 | 0 | 0 | 0 | 0 |
| 14 | 0.25 | 1 | 2 | 5 | 4 | 0 | 0 | 0 | 0 |
| 14 | 1.0 | 5 | 5 | 5 | 5 | 0 | 0 | 0 | 0 |
| 15 | 1.0 | 2 | 0 | 5 | 5 | 0 | 0 | 0 | 0 |
| 16 | 1.0 | 3 | 5 | 5 | 5 | 0 | 0 | 0 | 0 |
| 17 | 0.25 | 4 | 4 | 5 | 5 | — | — | — | — |
| 17 | 1.0 | 4 | 4 | 5 | 5 | 0 | 2 | 0 | 2 |
| 18 | 0.25 | 0 | 2 | 4 | 5 | — | — | — | — |
| 18 | 1.0 | 4 | 5 | 5 | 5 | 0 | 0 | 0 | 0 |
| 19 | 1.0 | 5 | 5 | 5 | 5 | — | — | — | — |
| 21 | 1.0 | 0 | 2 | 3 | 5 | 0 | 0 | 0 | 0 |
| 22 | 0.25 | 0 | 3 | 4 | 1 | — | — | — | — |
| 22 | 1.0 | 4 | 4 | 5 | 5 | 5 | 2 | 0 | 2 |
| 28 | 1.0 | 0 | 4 | 4 | 5 | 0 | 0 | 0 | 0 |
| 29 | 1.0 | 3 | 3 | 5 | 5 | 0 | 0 | 0 | 0 |
| 31 | 0.25 | 3 | 4 | 5 | 5 | — | — | — | — |
| 31 | 1.0 | 3 | 4 | 5 | 5 | 0 | 0 | 0 | 0 |
| 34 | 1.0 | 3 | 5 | 5 | 5 | 0 | 0 | 0 | 0 |
| 38 | 1.0 | 1 | 2 | 5 | 5 | 0 | 0 | 0 | 0 |
| 39 | 1.0 | 4 | 2 | 4 | 4 | 0 | 0 | 0 | 0 |

EXAMPLE 26

The post-emergent herbicidal activity of the compounds of the invention formulated as described in Example 24 was assessed by the following procedure.

The seeds of the test species werd sown in rows 2 cm deep in soil contained in seed boxes. The monocotyledonous plants and the dicotyledonous plants were down in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was remvoed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represnts 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 4

| Compound No | Application Rate (kg/ha) | Wh | Ot | Rg | Jm | P | Ip | Ms | Sf |
|---|---|---|---|---|---|---|---|---|---|
| 1 | 0.25 | 0 | 3 | 2 | 4 | — | — | — | — |
| 1 | 1.0 | 0 | 5 | 5 | 5 | 0 | 0 | 0 | 0 |
| 2 | 1.0 | 0 | 5 | 3 | 4 | 0 | 0 | 0 | 0 |
| 3 | 1.0 | 2 | 4 | 5 | 5 | 0 | 0 | 0 | 0 |
| 4 | 0.25 | 1 | 4 | 4 | 5 | — | — | — | — |
| 4 | 1.0 | 4 | 5 | 5 | 5 | 0 | 0 | 0 | 0 |
| 5 | 1.0 | 0 | 5 | 4 | 4 | 0 | 0 | 0 | 0 |
| 6 | 0.25 | 3 | 5 | 5 | 5 | — | — | — | — |
| 6 | 1.0 | 4 | 5 | 5 | 4 | 0 | 0 | 0 | 0 |
| 7 | 0.25 | 4 | 5 | 3 | 5 | — | — | — | — |
| 7 | 1.0 | 4 | 5 | 5 | 5 | 0 | 0 | 0 | 0 |
| 8 | 0.25 | 3 | 5 | 5 | 4 | — | — | — | — |
| 8 | 1.0 | 4 | 5 | 5 | 5 | 0 | 0 | 0 | 0 |
| 9 | 0.25 | 0 | 4 | 3 | 3 | — | — | — | — |
| 9 | 1.0 | 0 | 5 | 5 | 5 | 0 | 0 | 0 | 0 |
| 10 | 1.0 | 3 | 5 | 4 | 5 | 0 | 0 | 0 | 0 |
| 11 | 1.0 | 4 | 5 | 4 | 5 | 0 | 0 | 0 | 0 |
| 12 | 1.0 | 4 | 5 | 4 | 4 | 0 | 0 | 0 | 0 |
| 13 | 0.25 | 0 | 5 | 5 | 5 | 0 | 0 | 0 | 0 |

TABLE 4-continued

Post-emergent Herbicidal Activity

| Compound No | Application Rate (kg/ha) | Wh | Ot | Rg | Jm | P | Ip | Ms | Sf |
|---|---|---|---|---|---|---|---|---|---|
| 13 | 1.0 | 0 | 5 | 5 | 5 | 0 | 0 | 0 | 0 |
| 14 | 0.0625 | 1 | 5 | 4 | 4 | 0 | 0 | 0 | 0 |
| 14 | 0.25 | 5 | 5 | 5 | 5 | 0 | 0 | 0 | 0 |
| 14 | 1.0 | 5 | 5 | 5 | 5 | 0 | 0 | 0 | 0 |
| 15 | 0.25 | 1 | 1 | 3 | 5 | — | — | — | — |
| 15 | 1.0 | 1 | 3 | 5 | 5 | 0 | 0 | 0 | 0 |
| 16 | 0.25 | 4 | 5 | 4 | 4 | — | — | — | — |
| 16 | 1.0 | 4 | 5 | 5 | 4 | 0 | 0 | 0 | 0 |
| 17 | 0.0625 | 4 | 5 | 4 | 5 | — | — | — | — |
| 17 | 0.25 | 4 | 5 | 5 | 5 | — | — | — | — |
| 17 | 1.0 | 5 | 5 | 5 | 5 | 0 | 0 | 0 | 0 |
| 18 | 0.0625 | 4 | 5 | 4 | 5 | — | — | — | — |
| 18 | 0.25 | 5 | 5 | 5 | 5 | — | — | — | — |
| 18 | 1.0 | 5 | 5 | 5 | 5 | 0 | 0 | 0 | 0 |
| 19 | 0.0625 | 0 | 4 | 3 | 3 | — | — | — | — |
| 19 | 0.25 | 0 | 5 | 5 | 4 | — | — | — | — |
| 19 | 1.0 | 2 | 5 | 5 | 5 | 0 | 0 | 0 | 0 |
| 21 | 0.25 | 0 | 4 | 2 | 5 | — | — | — | — |
| 21 | 1.0 | 3 | 5 | 2 | 5 | 0 | 0 | 0 | 0 |
| 22 | 0.25 | 0 | 4 | 3 | 4 | — | — | — | — |
| 22 | 1.0 | 0 | 4 | 4 | 4 | 0 | 0 | 0 | 0 |
| 28 | 0.25 | 0 | 4 | 4 | 4 | — | — | — | — |
| 28 | 1.0 | 3 | 5 | 4 | 4 | 0 | 0 | 0 | 0 |
| 29 | 0.25 | 1 | 5 | 3 | 4 | — | — | — | — |
| 29 | 1.0 | 3 | 5 | 4 | 5 | 0 | 0 | 0 | 0 |
| 30 | 0.0625 | 0 | 5 | 2 | 0 | — | — | — | — |
| 30 | 0.25 | 0 | 5 | 4 | 4 | — | — | — | — |
| 30 | 1.0 | 4 | 5 | 5 | 5 | — | — | — | — |
| 31 | 0.25 | 0 | 5 | 2 | 4 | — | — | — | — |
| 31 | 1.0 | 2 | 5 | 5 | 5 | — | — | — | — |
| 32 | 1.0 | 0 | 0 | 4 | 4 | 0 | 0 | 0 | 0 |
| 34 | 0.25 | 1 | 4 | 3 | 5 | — | — | — | — |
| 34 | 1.0 | 2 | 5 | 5 | 5 | 0 | 0 | 0 | 0 |
| 36 | 1.0 | 0 | 2 | 4 | 4 | 0 | 0 | 0 | 0 |
| 37 | 1.0 | 1 | 5 | 4 | 3 | 0 | 0 | 0 | 0 |
| 38 | 0.25 | 0 | 4 | 3 | 4 | 0 | 0 | 0 | 0 |
| 38 | 1.0 | 0 | 5 | 5 | 5 | 0 | 0 | 0 | 0 |
| 39 | 1.0 | 0 | 4 | 4 | 4 | 0 | 0 | 0 | 0 |
| 40 | 0.25 | 0 | 3 | 2 | 4 | — | — | — | — |
| 40 | 1.0 | 1 | 5 | 3 | 4 | 0 | 0 | 0 | 0 |
| 41 | 0.25 | 1 | 4 | 4 | 4 | — | — | — | — |
| 41 | 1.0 | 3 | 5 | 5 | 5 | 0 | 0 | 0 | 0 |
| 42 | 1.0 | 1 | 5 | 5 | 5 | 0 | 0 | 0 | 0 |

EXAMPLE 27

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade mark for a surface-active agent comprising a condensate of sorbitan monolaurate with 20 molar proportions of ethylene oxide. Each 5 ml emulsion containing a test compound was then diluted to 40 ml with water and sprayed on to young pot plants (postemergence test) of the species named in Table 5 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 5 below. A dash (-) means that no experiment was carried out.

The names of the test plants were as follows:
Mz: Maize
Ww: Winter wheat
Rc: Rice
Br: Barley
Av: *Avena fatua*
Dg: *Digitaria sanguinalis*
Al: *Alopecurus myosuroides*
St: *Setaria viridis*
Ec: *Echinochloa crus-galli*
Sh: *Sorghum halepense*
Ag: *Agropyron repens*

TABLE 5

| Compound No | Application Method | Rate (kg/ha) | Mz | Ww | Rc | Br | Av | Dg | Al | St | Ec | Sh | Ag |
|---|---|---|---|---|---|---|---|---|---|---|---|---|---|
| 1 | POST | 0.4 | 4 | 4 | 4 | 4 | 4 | 4 | 4 | 4 | 4 | 4 | 4 |
| 1 | POST | 0.2 | 4 | 4 | 4 | 4 | 4 | 4 | 4 | 4 | 4 | 4 | 4 |
| 1 | POST | 0.1 | 4 | 2 | 4 | 4 | 4 | 4 | 4 | 4 | 4 | 3 | 3 |
| 1 | POST | 0.05 | 2 | 0 | 4 | 3 | 4 | 3 | 3 | 3 | 3 | 2 | 2 |
| 5 | POST | 0.8 | 4 | 4 | 4 | 4 | 5 | 4 | 4 | 4 | 5 | 4 | 4 |
| 5 | POST | 0.4 | 4 | 4 | 2 | 4 | 4 | 3 | 4 | 4 | 4 | 4 | 4 |
| 5 | POST | 0.2 | 4 | 4 | 0 | 4 | 4 | 3 | 4 | 4 | 4 | 4 | 4 |
| 5 | POST | 0.1 | 4 | 1 | 4 | 4 | 4 | 1 | 4 | 4 | 4 | 3 | 4 |
| 6 | POST | 0.8 | 4 | 2 | 2 | 4 | 4 | 3 | 3 | 4 | 4 | 4 | 2 |
| 6 | POST | 0.4 | 4 | 1 | 0 | 2 | 4 | 3 | 4 | 4 | 4 | 3 | 2 |
| 6 | POST | 0.2 | 4 | 0 | 0 | 2 | 4 | 2 | 3 | 4 | 4 | 3 | 0 |
| 6 | POST | 0.1 | 2 | 0 | 0 | 2 | 4 | 1 | 2 | 2 | 4 | 2 | 0 |
| 7 | POST | 0.8 | 5 | 4 | 3 | 4 | 5 | 4 | 4 | 5 | 5 | 4 | 4 |
| 7 | POST | 0.4 | 5 | 4 | 4 | 4 | 4 | 4 | 4 | 5 | 5 | 4 | 4 |
| 7 | POST | 0.2 | 4 | 4 | 0 | 4 | 5 | 4 | 4 | 4 | 5 | 4 | 3 |
| 7 | POST | 0.1 | 3 | 0 | 4 | 4 | 3 | 3 | 3 | 4 | 4 | 4 | 2 |
| 8 | POST | 0.8 | 4 | 4 | 4 | 4 | 5 | 4 | 4 | 4 | 4 | 4 | 4 |
| 8 | POST | 0.4 | 4 | 4 | 4 | 4 | 4 | 4 | 4 | 4 | 4 | 4 | 3 |
| 8 | POST | 0.2 | 4 | 4 | 2 | 4 | 4 | 4 | 4 | 4 | 4 | 4 | 3 |
| 8 | POST | 0.1 | 4 | 0 | 1 | 2 | 4 | 0 | 4 | 3 | 4 | 3 | 0 |
| 10 | POST | 0.8 | 4 | 4 | 4 | 4 | 5 | 5 | 4 | 4 | 5 | 4 | 4 |
| 10 | POST | 0.4 | — | 4 | 4 | 4 | 4 | 4 | 4 | 4 | 4 | 4 | 3 |
| 10 | POST | 0.2 | 4 | 4 | 4 | 4 | 4 | 4 | 4 | 4 | 4 | 4 | 3 |
| 10 | POST | 0.1 | 2 | 0 | 0 | 3 | 4 | 1 | 0 | 2 | 4 | 1 | 0 |
| 11 | POST | 0.8 | 4 | 4 | 4 | 4 | — | — | — | — | — | — | — |
| 11 | POST | 0.4 | 4 | 2 | 4 | 4 | — | — | — | — | — | — | — |
| 11 | POST | 0.2 | 4 | 0 | 4 | 4 | 4 | 4 | 4 | 4 | 4 | — | 3 |

TABLE 5-continued

| Compound No | Application Method | Rate (kg/ha) | Mz | Ww | Rc | Br | Av | Dg | Al | St | Ec | Sh | Ag |
|---|---|---|---|---|---|---|---|---|---|---|---|---|---|
| 11 | POST | 0.1 | 4 | 0 | 3 | 1 | 4 | 4 | 4 | 4 | 3 | 3 | 0 |
| 13 | POST | 0.4 | 4 | 2 | 4 | 4 | 4 | 5 | 4 | 4 | 4 | 4 | 3 |
| 13 | POST | 0.2 | 4 | 0 | 3 | 4 | 4 | 5 | 4 | 4 | 4 | 4 | 1 |
| 13 | POST | 0.1 | 4 | 2 | 3 | 4 | 3 | 4 | 4 | 4 | 4 | 4 | 1 |
| 13 | POST | 0.05 | 4 | 0 | 0 | 3 | 0 | 4 | 2 | 2 | 4 | 3 | 0 |
| 14 | POST | 0.2 | 5 | 4 | 4 | 4 | 5 | 4 | 5 | 4 | 5 | 5 | 3 |
| 14 | POST | 0.1 | 5 | 3 | 2 | 4 | 5 | 4 | 5 | 4 | 5 | 5 | 0 |
| 14 | POST | 0.05 | 5 | 1 | 0 | 4 | 5 | 3 | 4 | 4 | 5 | 5 | 0 |
| 15 | POST | 0.2 | 4 | 0 | 2 | 2 | 1 | 2 | 0 | 4 | 4 | 4 | 2 |
| 15 | POST | 0.1 | 4 | 0 | 0 | 4 | 0 | 2 | 0 | 4 | 4 | 3 | 1 |
| 16 | POST | 0.2 | 5 | 4 | 2 | 4 | 5 | 5 | 4 | 4 | 4 | 4 | 4 |
| 16 | POST | 0.1 | 4 | 4 | 2 | 4 | 4 | 4 | 4 | 4 | 4 | 2 | 3 |
| 16 | POST | 0.05 | 4 | 3 | 1 | 4 | 4 | 4 | 4 | 4 | 4 | 1 | 1 |
| 16 | POST | 0.02 | 4 | 0 | 0 | 3 | 4 | 4 | 3 | 4 | 3 | 0 | 0 |
| 17 | POST | 0.2 | 5 | 4 | 3 | 5 | 5 | 5 | 4 | 5 | 5 | 4 | 2 |
| 17 | POST | 0.1 | 5 | 4 | 0 | 5 | 5 | 5 | 5 | 5 | 5 | 3 | 2 |
| 17 | POST | 0.05 | 4 | 0 | 0 | 4 | 4 | 5 | 4 | 4 | 4 | 3 | 0 |
| 17 | POST | 0.02 | 4 | 0 | 0 | 3 | 4 | 4 | 3 | 4 | 3 | 1 | 0 |
| 18 | POST | 0.2 | 5 | 4 | 3 | 5 | 5 | 5 | 5 | 5 | 5 | 5 | 4 |
| 18 | POST | 0.1 | 5 | 4 | 3 | 5 | 5 | 5 | 4 | 5 | 5 | 5 | 2 |
| 18 | POST | 0.05 | 5 | 0 | 1 | 4 | 4 | 5 | 4 | 5 | 5 | 4 | 0 |
| 18 | POST | 0.02 | 4 | 0 | 0 | 2 | 4 | 5 | 3 | 4 | 4 | 2 | 0 |
| 21 | POST | 0.2 | 4 | 0 | 4 | 4 | 4 | 3 | 4 | 4 | 4 | 4 | 1 |
| 21 | POST | 0.1 | 4 | 0 | 4 | 4 | 2 | 2 | 3 | 4 | 4 | 2 | 2 |
| 21 | POST | 0.05 | 2 | 0 | 0 | 1 | 2 | 1 | 0 | 3 | 4 | 2 | 0 |
| 29 | POST | 0.2 | 5 | 1 | 4 | 3 | 4 | 4 | 4 | 4 | 4 | 4 | 2 |
| 29 | POST | 0.1 | 4 | 0 | 4 | 3 | 4 | 4 | 4 | 4 | 4 | 4 | 1 |
| 29 | POST | 0.05 | 4 | 0 | 2 | 1 | 2 | 3 | 4 | 3 | 4 | 4 | 1 |
| 30 | POST | 0.2 | 4 | 1 | 1 | 4 | 4 | 4 | 3 | 4 | 3 | 4 | 2 |
| 30 | POST | 0.1 | 3 | 0 | 1 | 3 | 4 | 4 | 4 | 3 | 3 | 4 | 1 |
| 31 | POST | 0.2 | 4 | 3 | 2 | 4 | 4 | 4 | 3 | 4 | 3 | 4 | 0 |
| 31 | POST | 0.1 | 4 | 0 | 1 | 3 | 4 | 4 | 3 | 3 | 3 | 4 | 1 |
| 31 | POST | 0.05 | 4 | 0 | 0 | 2 | 3 | 4 | 3 | 3 | 2 | 3 | 1 |
| 34 | POST | 0.4 | 4 | 1 | 3 | 4 | 4 | 3 | 4 | 4 | 5 | 4 | 0 |
| 34 | POST | 0.2 | 4 | 0 | 2 | 4 | 4 | 1 | 4 | 4 | 4 | 3 | 0 |
| 34 | POST | 0.1 | 3 | 0 | 1 | 3 | 4 | 0 | 3 | 3 | 4 | 1 | 0 |
| 36 | POST | 0.8 | 4 | 0 | 1 | 4 | 4 | 4 | 4 | 4 | 4 | 4 | 2 |
| 36 | POST | 0.4 | 4 | 1 | 0 | 4 | 4 | 4 | 4 | 4 | 4 | 4 | 0 |
| 36 | POST | 0.2 | 2 | 0 | 1 | 4 | 0 | 4 | 4 | 0 | 4 | 4 | 0 |
| 37 | POST | 0.4 | 3 | 0 | 2 | 0 | 4 | 3 | 4 | 3 | 2 | 0 | 0 |
| 38 | POST | 0.4 | 4 | 0 | 4 | 4 | 4 | 2 | 4 | 3 | 4 | 3 | 0 |
| 38 | POST | 0.2 | 4 | 0 | 3 | 3 | 4 | 1 | 3 | 3 | 4 | 2 | 0 |
| 39 | POST | 0.4 | 5 | 1 | 5 | 4 | 5 | 3 | 5 | 5 | 5 | 3 | 2 |
| 39 | POST | 0.2 | 4 | 1 | 5 | 4 | 5 | 2 | 5 | 5 | 5 | 1 | 2 |
| 39 | POST | 0.1 | 2 | 0 | 3 | 4 | 4 | 1 | 4 | 4 | 5 | 0 | 0 |
| 40 | POST | 0.4 | 4 | 0 | 0 | 4 | 4 | 4 | 4 | 4 | 4 | 4 | 2 |
| 40 | POST | 0.2 | 4 | 0 | 0 | 3 | 3 | 3 | 3 | 3 | 4 | 3 | 0 |
| 41 | POST | 0.4 | 5 | 1 | 4 | 5 | 5 | 5 | 5 | 5 | 4 | 4 | 0 |
| 41 | POST | 0.2 | 5 | 0 | 4 | 3 | 4 | 5 | 5 | 4 | 3 | 1 | 1 |
| 41 | POST | 0.1 | 4 | 0 | 4 | 2 | 4 | 5 | 4 | 4 | 4 | 2 | 0 |

We claim:
1. A compound of formula I,

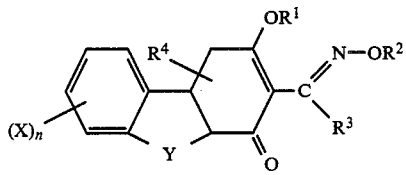

wherein:
Y is a linking group selected from the group consisting of:
—(CH$_2$)$_l$—; —CH(CH$_3$)—; —C(CH$_3$)$_2$—; —CH(CH$_3$)CH$_2$—;
—G(CH$_2$)$_m$—; —CH$_2$GCH$_2$—; —C(G)(CH$_2$)$_m$—; —GC(G)—; and —NHC(G)—;
wherein:
G is selected from oxygen and sulfur;
l is an integer selected from 1 to 3; and
m is zero or an integer selected from 1 and 2;
n is zero or an integer selected from 1 to 4;
X, which may be the same or different, are independently selected from the group consisting of: halogen; nitro; cyano; C$_1$ to C$_6$ alkyl; C$_1$ to C$_6$ alkyl substituted with halogen or cyano; hydroxy; C$_1$ to C$_6$ alkoxy; C$_1$ to C$_6$ alkylthio; sulfamoyl; N—(C$_1$ to C$_6$ alkyl)sulfamoyl; N,N-di(C$_1$ to C$_6$ alkyl)sulfamoyl; the group —(CH$_2$)$_p$C(=A)Z wherein p is zero or one, A is selected from oxygen and sulfur, and Z is selected from the group consisting of hydrogen, hydroxy, C$_1$ to C$_6$ alkoxy, C$_1$ to C$_6$ alkylthio, amino, N-(C$_1$ to C$_6$ alkyl) amino, N,N-di(C$_1$ to C$_6$ alkylamino, N-(C$_1$ to C$_6$ alkanoyl)amino, C$_1$ to C$_6$ alkyl, and C$_1$ to C$_6$ haloalkyl; the group —NR$^5$R$^6$ wherein R$^5$ and R$^6$ are independently selected from the group consisting of hydrogen, C$_1$ to C$_6$ alkyl, C$_2$ to C$_6$ alkanoyl, C$_2$ to C$_6$ haloalkanoyl, C$_1$ to C$_6$ alkylsulfonyl, and benzoyl; the group —NHC(=B)NR$^7$R$^8$ wherein B is selected from oxygen and sulfur and R$^7$ and R$^8$ are independently selected from hydrogen and C$_1$ to C$_6$ alkyl;

and the group —(CH$_2$)$_q$— which bridges two adjacent carbon atoms of the benzene ring and wherein q is an integer selected from 3 or 4;

R$^1$ is selected from the group consisting of: hydrogen; an acyl group; and an inorganic or organic cation;

R$^2$ is selected from the group consisting of: C$_1$ to C$_6$ alkyl; C$_2$ to C$_6$ alkenyl; C$_2$ to C$_6$ haloalkenyl; C$_2$ to C$_6$ alkynyl; C$_3$ to C$_6$ haloalkynyl; and substituted C$_1$ to C$_6$ alkyl wherein the alkyl group is substituted with a substituent selected from the group consisting of halogen, C$_1$ to C$_6$ alkoxy, C$_1$ to C$_6$ alkylthio, phenyl and substituted phenyl wherein the benzene ring is substituted with from one to three substituents selected from the group consisting of halogen, C$_1$ to C$_6$ alkyl, C$_1$ to C$_6$ haloalkyl, C$_1$ to C$_6$ alkoxy, and C$_1$ to C$_6$ alkylthio;

R$^3$ is selected from the group consisting of: C$_1$ to C$_6$ alkyl; C$_1$ to C$_6$ fluoroalkyl; C$_2$ to C$_6$ alkenyl; C$_2$ to C$_6$ alkynyl; and phenyl; and R$^4$ is selected from the group consisting of: hydrogen; halogen; cyano; C$_1$ to C$_6$ alkyl; and (C$_1$ to C$_6$ alkoxy) carbonyl.

2. A Compound according to claim 1 wherein: Y is a linking group selected form the group consisting of:
—(CH$_2$)$_l$—; —CH(CH$_3$)—; —C(CH$_3$)$_2$—; —CH(CH$_3$)CH$_2$—;
—G(CH$_2$)$_m$—; —CH$_2$GCH$_2$—; —C(G)(CH$_2$)$_m$—; —GC(G)—; and
G—NHC(G)—;
wherein:
G is selected from oxygen and sulfur;
l is an integer selected from 1 to 3; and
m is zero or an integer selected from 1 and 2;
n is zero or an integer selected from 1 to 4;

X, which may be the same or different, are independently selected from the group consisting of: halogen; nitro; cyano; C$_1$ to C$_6$ alkyl; C$_1$ to C$_6$ alkyl substituted with halogen or cyano; hydroy; C$_1$ to C$_6$ alkoxy; C$_1$ to C$_6$ alkylthio; sulfamoyl; N-(C$_1$ to C$_6$ alkyl)sulfamoyl; N,N-di(C$_1$ to C$_6$ alkyl)sulfamoyl; the group —(CH$_2$)$_p$C(=A)Z wherein p is zero or one, A is selected from oxygen and sulfur, and Z is selected from the group consisting of hydrogen, hydroxy, C$_1$ to C$_6$ alkoxy, C$_1$ to C$_6$ alkylthio, amino, N-(C$_1$ to C$_6$ alkyl)amino, N,N-di(C$_1$ to C$_6$ alkyl)amino, N-(C$_1$ to C$_6$ alkanoyl)amino, C$_1$ to C$_6$ alkyl, and C$_1$ to C$_6$ haloalkyl; the group —NR$^5$R$^6$ wherein R$^5$ and R$^6$ are independently selected from the group consisting of hydrogen, C$_1$ to C$_6$ alkyl, C$_2$ to C$_6$ alkanoyl, C$_2$ to C$_6$ haloalkanoyl, C$_1$ to C$_6$ alkylsulfonyl, and benzoyl; the group —NHC(=B)NR$^7$R$^8$ wherein B is selected from oxygen and sulfur and R$^7$ and R$^8$ are independently selected from hydrogen and C$_1$ to C$_6$ alkyl; and the group —(CH$_2$)$_q$— which bridged two adjacent carbon atoms of the benzene ring and wherein q is an integer selected from 3 or 4;

R$^1$ is selected from the group consisting of: hydrogen; C$_2$ to C$_6$ alkanoyl; benzoyl and substituted benzoyl wherein the benzene ring is substituted with from one to three substituents selected from the group consisting of halogen, nitro, C$_1$ to C$_6$ alkyl and C$_1$ to C$_6$ alkoxy; benzenesulfonyl and substituted benzenesulfonyl wherein the benzene ring is substituted with from one to three substituents selected from the group consisting of halogen, nitro, C$_1$ to C$_6$ alkyl and C$_1$ C$_6$ alkoxy; and an inorganic or an organic cation selected from the alkali metals, the alkaline earth metals the transition metals the ammonium ion and the tri- and tetra(alkyl) ammonium ions wherein alkyl is selected from C$_1$ to C$_6$ alkyl and C$_1$ to C$_6$ hydroxyalkyl;

R$^2$ is selected from the group consisting of: C$_1$ to C$_6$ alkyl; C$_2$ to C$_6$ alkenyl; C$_2$ to C$_6$ haloalkenyl; C$_2$ to C$_6$ alkynyl, C$_3$ to C$_6$ haloalkynyl; and substituted C$_1$ to C$_6$ alkyl wherein the alkyl group is substituted with a substituent selected from the group consisting of halogen, C$_1$ to C$_6$ alkoxy, C$_1$ to C$_6$ alkylthio, phenyl and substituted phenyl wherein the benzene ring is substituted with from one to three substituents selected from the group consisting of halogen, C$_1$ to C$_6$ alkyl, C$_1$ to C$_6$ haloalkyl, C$_1$ to C$_6$ alkoxy, and C$_1$ to C$_6$ alkylthio;

R$^3$ is selected from the group consisting of: C$_1$ to C$_6$ alkyl; C$_1$ to C$_6$ fluoroalkyl; C$_2$ to C$_6$ alkenyl; C$_2$ to C$_6$ alkynyl; and phenyl; and R$_4$ is selected from the group consisting of: hydrogen; halogen; cyano; C$_1$ to C$_6$ alkyl; and (C$_1$ to C$_6$ alkoxy) carbonyl.

3. A compound according to claim 2 wherein:
Y is a linking group selected form the group consisting of:
—(CH$_2$)$_l$—; —CH(CH$_3$)—; —C(CH$_3$)$_2$—; —CH(CH$_3$)CH$_2$—;
—G(CH$_2$)$_m$—; —CH$_2$GCH$_2$—; —C(G)(CH$_2$)$_m$—; —GC(G)—; and
—NHC(G)—;
wherein:
G is selected from oxygen and sulfur;
l is an integer selected from 1 to 3; and
m is zero or an integer selected from 1 and 2;
n is zero or an integer selected from 1 to 4;

X, which may be the same or different, are independently selected from the group consisting of: halogen; nitro; cyano; C$_1$ to C$_6$ alkyl; C$_1$ to C$_6$ alkoxy; C$_1$ to C$_6$ alkylthio; sulfamoyl; N-(C$_1$ to C$_6$ alkyl)- sulfamoyl; N,N-di(C$_1$ to C$_6$ alkyl)sulfamoyl; the group -(CH$_2$)$_p$C(=A)Z wherein p is zero or one, A is selected from oxygen and sulfur, and Z is selected from the group consisting of hydrogen, hydroxy, C1 to C6 alkoxy, C$_1$ to C$_6$ alkylthio, amino, N-(C$_1$ to C$_6$ alkyl)amino, N,N-di(C$_1$ to C$_6$ alkyl)amino, N-(C$_1$ to C$_6$ alkanoyl)amino, C$_1$ to C$_6$ alkyl, and C$_1$ to C$_6$ haloalkyl; the group —NR$^5$R$^6$ wherein R$^5$ and R$^6$ are independently selected from the group consisting of hydrogen, C$_1$ to C$_6$ alkyl, C$_2$ to C$_6$ alkanoyl, C$_2$ to C$_6$ haloalkanoyl, C$_1$ to C$_6$ alkylsulfonyl, and benzoyl; the group —NHC(=B)NR$^7$R$^8$ wherein B is selected from oxygen and sulfur and R$^7$ and R$^8$ are independently selected from hydrogen and Chd 1 to C$_6$ alkyl; and the group (CH$_2$)q- which bridges two adjacent carbon atoms of the benzene ring and wherein q is an integer selected from 3 or 4;

R$^1$, is selected from the group consisting of: hydrogen; C$_1$ to C$_6$ alkanoyl; benzoyl and substituted benzoyl wherein the benzene ring is substituted with from one to two substituents selected from the group consisting of halogen, nitro, C$_1$ to C$_6$ alkyl and C$_1$ to C$_6$ alkoxy; an alkali metal cation; an alkaline earth cation; a transition metal cation; the ammonium ion and the tri and tetra(alkyl) ammonium ions wherein alkyl is selected from C$_1$ to C$_6$ alkyl and C$^1$ to C$^6$ hydroxy-alkyl;

R$^2$ is selected from the group consisting of C$_1$ to C$_6$ alkyl, C$_1$ to C$_6$ haloalkyl, C$_2$ to C$_6$ alkenyl, C$_2$ to C$_6$ haloalkenyl and C$_3$ to C$_6$ alkynyl;

R$^3$ is selected from the group consisting of C$_1$ to C$_6$ alkyl;

$R^4$ is selected from the group consisting hydrogen, halogen, $C_1$ to $C_6$ alkyl; and ($C_1$ to $C_6$ alkoxy) carbonyl.

4. A compound according to claim 3 wherein:

Y is a linking group selected form the group consisting of:

—$(CH_2)_l$—; —$CH(CH_3)$—; —$C(CH_3)_2$—; —$CH(CH_3)CH_2$—;

—$G(CH_2)_m$—; —$CH_2GCH_2$—; —$C(G)(CH_2)_m$—; —$GC(G)$—; and —$NHC(G)$—;

wherein:

G is selected from oxygen and sulfur;

l is an integer selected from 1 to 3; and m is zero or an integer selected from 1 and 2;

n is zero or an integer selected from 1 to 4;

X, which may be the same or different, are independently selected from the group consisting of: halogen; nitro; $C_1$ to $C_6$ alkyl; $C_1$ to $C_6$ alkoxy; $C_1$ to $C_6$ alkylthio; sulfamoyl; N-($C_1$ to $C_6$ alkyl)sulfamoyl; N,N-di($C_1$ to $C_6$ alkyl) sulfamoyl; the group —$(CH_2)_p$—$C(=A)Z$ wherein p is zero or one, A is either oxygen or sulfur, and Z is selected from the group consisting of hydroxy, $C_1$ to $C_6$ alkoxy, $C_1$ to $C_6$ alkylthio, amino, N-($C_1$ to $C_6$ alkyl) amino, N,N-di($C_1$ to $C_6$ alkyl) amino, $C_1$ to $C_6$ alkyl and $C_1$ to $C_6$ haloalkyl; the group —$NR^5R^6$ wherein $R_5$ and $R_6$ are independently selected from the group consisting of hydrogen, $C_1$ to $C_6$ alkyl, $C_2$ to $C_6$ alkanoyl, $C_2$ to $C_6$ haloalkanoyl, $C_1$ to $C_6$ alkylsulfonyl; and the group —$(CH_2)_q$—which bridges two adjacent carbon atoms of the benzene ring and wherein q is an integer selected from 3 or 4;

$R_1$ is selected from the group consisting of hydrogen; $C_2$ to $C_6$ alkanoyl; benzoyl and substituted benzoyl wherein the benzene ring is substituted with from one to two substituents selected from the group consisting of halogen, nitro, $C_1$ to $C_6$ alkyl and $C_1$ to $C_6$ alkoxy; an alkali metal cation; an alkaline earth cation; a transition metal cation; the ammonium ion and the tri and tetra(alkyl) ammonium ions wherein alkyl is selected from $C_1$ to $C_6$ alkyl and $C_1$ to $C_6$ hydroxy alkyl;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ is selected from the group consisting of $C_1$ to $C_6$ alkyl; and $R^4$ is hydrogen.

5. A compound according to claim 4 wherein:

Y is a linking group selected form the group consisting of:

—$(CH_2)_l$—; —$G(CH_2)_m$—; —$CH_2GCH_2$—; —$C(G)(CH_2)_m$—; and —$GC(G)$—;

wherein:

G is selected from oxygen and sulfur;

l is an integer selected from 1 to 3; and m is zero or an integer selected from 1 and 2;

n is zero or an integer selected from 1 to 4;

X, which may be the same or different, are independently selected from the group consisting of halogen; $C_1$ to $C_6$ alkyl; $C_1$ to $C_6$ alkoxy, $C_1$ to $C_6$ alkylthio; sulfamoyl; N-($C_1$ to $C_6$ alkyl) sulfamoyl; N,N-di($C_1$ to $C_6$ alkyl) sulfamoyl; ($C_2$ to $C_6$ alkanoyl; $C_2$ to $C_6$ haloalkanoyl; and $C_2$ to $C_6$ haloalkanoylamino;

$R_1$ is selected form the group consisting of: hydrogen; $C_2$ to $C_6$ alkanoyl; benzoyl; an alkali metal cation; an alkaline earth metal cation; a transition metal cation; the ammonium ion and the tri and tetra (alkyl) ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ is selected from the group consisting of $C_2$ to $C_6$ alkyl; and $R^4$ is hydrogen.

6. A compound according to claim 5 wherein:

Y is a linking group selected from the group consisting of:

—$CH_2$—; —$CH_2CH_2$—; —$CH_2CH_2CH_2$—; —O—; —S—;

—$O$—$CH_2$—; —$OCH_2CH_2$—; —$SCH_2$—;

—$CH_2OCH_2$—; —$CH_2SCH_2$—; —CO—;

—$COCH_2$—; —$COCH_2CH_2$—; and —OCO—;

n is zero or an integer selected from 1 to 4;

X, which may be the same or different, are independently selected from the group consisting of halogen; $C_1$ to $C_6$ alkyl; $C_1$ to $C_6$ alkoxy; sulfamoyl; N-($C_1$ to $C_6$ alkyl) sulfamoyl; N,N-di($C_1$ to $C_6$ alkyl) sulfamoyl and $C_2$ to $C_6$ alkanoyl;

$R^1$ is selected from the group consisting of hydrogen; $C_2$ to $C_6$ alkanoyl; benzoyl, the alkali metal cations; the alkaline earth metal cations and the transition metal cations;

$R^2$ is selected from the group consisting of $C_1$ to $C_6$ alkyl, $C_1$ to $C_6$ halo alkyl, $C_2$ to $C_6$ alkenyl, $C_2$ to $C_6$ haloalkenyl and $C_3$ to $C_6$ alkynyl;

$R^3$ is selected from $C_1$ to $C_6$ alkyl; and $R^4$ is hydrogen.

7. A compound according to claim 6 wherein:

Y is a linking group selected from the group consisting of:

—$CH_2$—; —$CH_2CH_2$—; —$CH_2CH_2CH_2$—; —O—;

—$OCH_2$—; —$OCH_2CH_2$—; —$SCH_2$—; and —$COCH_2$—;

n is zero or an integer selected from 1 to 4;

X, which may be the same or different, are independently selected from the group consisting of $C_1$ to $C_6$ alkyl; $C_1$ to $C_6$ alkoxy; N($C_1$ to $C_6$ alkyl) sulfamoyl; N,N-di ($C_1$ to $C_6$ alkyl) sulfamoyl and $C_1$ to $C_6$ alkanoyl;

$R^1$ is selected from the group consisting of hydrogen; $C_2$ to $C_6$ alkanoyl; benzoyl; the alkali metal cations; the alkaline earth metal cations and the transition metal cations;

$R^2$ is selected from $C_1$ to $C_4$ alkyl, $C_1$ to $C_4$ haloalkyl, $C_2$ to $C_4$ alkenyl, $C_2$ to $C_4$ haloalkenyl and $C_3$ to $C_4$ alkynyl;

$R^3$ is selected from $C_1$ to $C_4$ alkyl; and $R^4$ is hydrogen.

8. A compound according to claim 7 wherein:

Y is a linking group selected from the group consisting of:

—$CH_2$—; —$CH_2CH_2$—; —$CH_2CH_2CH_2$—; —O—;

—$OCH_2$—; —$OCH_2CH_2$—; —$SCH_2$—; and —$COCH_2$—;

n is zero or an integer selected from 1 to 4;

X, which may be the same or different, are independently selected from the group consisting of methyl, methoxy N-methylsulfamoyl, N,N-dimethyl-sulfamoyl, acetyl and propionyl;

$R^1$ is selected from the group consisting of hydrogen, $C_2$ to $C_6$ alkanoyl, and the alkali metal cations;

$R^2$ is selected from the group consisting of $C_1$ to $C_3$ alkyl, 2-haloethyl, allyl, 3-halo-allyl and propargyl; and $R^3$ is selected from $C_1$ to $C_4$ alkyl; and
$R^4$ is hydrogen.

9. A compound according to claim 1 selected from the group consisting of:

2-[1-(Ethoxyimino)propyl]-5,6,7,8-tetramethyl-1,3-dioxa-1,2,3,4,4a,9,10,10a-octahydrophenanthrene;

2-[1-(Ethoxyimino)propyl]-5,8-dimethyl-6,7-trimethylene-1,3-dioxa-1,2,3,4,4a,9,10,10a-octahydrophenanthrene;

2-[1-(Ethoxyimino)propyl]-5,6,7-trimethyl-1,3-dioxa-1,2,3,4,4a,9,10,10a-octahydrophenanthrene;

8-Acetyl-2-[ethoxyimino)propyl]-5,6,7-trimethyl-1,3-dioxa-1,2,3,4,4a,9,10,10a-octahydrophenanthrene.

10. A herbicidal composition comprising as active ingredient a herbicidally effective amount of a compound as defined according to claim 1 and an inert carrier therefor.

11. A process for severely damaging or killing unwanted plants which process comprises applying to said plants, or to the growth medium of said plants, an effective amount of a compound as defined according to claim 1 or an effective amount of a composition as defined according to claim 10.

12. A process for selectively controlling the growth of monocotyledonous weeds in dicotyledonous crops which process comprises applying to said crop, or to the growth medium of said crop, a compound as defined according to claim 1 or a composition as defined according to claim 10 in a amount sufficient to severely damage or kill said weeds but insufficient to substantially damage said crop.

13. A process according to claim 11 or claim 12 wherein the compound is applied at a rate in the range of from 0.005 to 20 kilograms per hectare.

* * * * *